United States Patent [19]

Goldenberg

[11] Patent Number: 5,686,578
[45] Date of Patent: Nov. 11, 1997

[54] POLYSPECIFIC IMMUNOCONJUGATES AND ANTIBODY COMPOSITES FOR TARGETING THE MULTIDRUG RESISTANT PHENOTYPE

[75] Inventor: David M. Goldenberg, Mendham, N.J.

[73] Assignee: Immunomedics, Inc., Morris Plains, N.J.

[21] Appl. No.: 286,430

[22] Filed: Aug. 5, 1994

[51] Int. Cl.$^6$ .................. C07K 16/00; C07K 16/18; C07K 16/28; C07K 16/12
[52] U.S. Cl. .................. 530/387.3; 530/391.1; 530/391.9; 530/389.7; 530/389.5; 530/388.8; 530/388.85; 530/389.1; 530/388.2; 530/388.4
[58] Field of Search .................. 530/387.3, 391.1–391.9, 530/389.7, 389.5, 388.8, 388.85, 389.1, 388.2, 388.4

[56] References Cited

U.S. PATENT DOCUMENTS

| | | | |
|---|---|---|---|
| 5,005,588 | 4/1991 | Rubin | 128/804 |
| 5,258,372 | 11/1993 | Levy | 514/154 |
| 5,332,567 | 7/1994 | Goldenberg | 424/1.49 |

FOREIGN PATENT DOCUMENTS

| | | |
|---|---|---|
| 2093866 | 10/1993 | Canada. |
| 0 569 141 | 11/1993 | European Pat. Off.. |
| WO 92/08802 | 5/1992 | WIPO. |
| WO 93/02105 | 2/1993 | WIPO. |
| WO 93/19094 | 9/1993 | WIPO. |
| WO 93/25700 | 12/1993 | WIPO. |

OTHER PUBLICATIONS

Bray et al. "Malaria Chemotherapy: Resistance to Quinoline Containing Drugs in Plasmodium Falciparum", *FEMS Microbiol. Lett.* 113:1–8 (1993).
Calabresi "Drug Resistance: Lonidamine," *PPO Updates* 8(6):1–15 (Jun. 1994).
Chen et al. "Internal Duplication and Homology with Bacterial Transport Proteins in the mdr1 (P–Glycoprotein) Gene from Multidrug–Resistant Human Cells", *Cell* 47:318–389 (Nov. 7, 1986).
Childs et al. "The MDR Superfamily of Genes and Its Biological Implications," *Important Advances in Oncology* De Vita et al. (Eds.) pp. 21–36 (J.P. Lippincott 1994).
Dalton et al. "Immunohistochemical Detection and Quantitation of P–Glycoprotein in Multiple Drug–Resistant Human Myeloma Cells: Association With Level of Drug Resistance and Drug Accumulation", *Blood* 73:747–752 (Feb. 15, 1989).
DeYoung "Biotech Companies and Drug Firms Take Steps to Combat Drug–Resistant Bacteria", *Genetic Engineering News* 14:1, 14 (Jul. 14, 1994).
Doige et al. "ATP–Dependent Transport Systems in Bacteria and Humans: Relevance to Cystic Fibrosis and Multidrug Resistance", *Annu. Rev. Microbiol.* 47:291–319 (1993).
Durrant et al. "Sensitivity of Newly Established Colorectal Cell Lines to Cytotoxic Drugs and Monoclonal Antibody Drug Conjugates", *Br. J. Cancer* 56:722–726 (1987).

Efferth et al. "Antibody–Directed Therapy of Multidrug–Resistant Tumor Cells", *Med. Oncol. & Tumor Pharmacother.* 9(1):11–19 (1992).
Endicott et al. "The Biochemistry of P–Glycoprotein–Mediated Multidrug Resistance", *Annu. Rev. Biochem.* 58:137–171 (1989).
FitzGerald et al. "A Monoclonal Antibody–Pseudomonas Toxin Conjugate That Specifically Kills Multidrug–Resistant Cells", *Proc. Natl. Acad. Sci. USA* 84:4288–4292 (Jun. 1987).
Georges et al. "Modulation of ATP and Drug Binding By Monoclonal Antibodies Against P–Glycoprotein", *J. Cell. Physiol.* 148:479–484 (1991).
Goldstein et al. "Expression of a Multidrug Resistance Gene in Human Cancers", *J. Natl. Cancer Inst.* 81: 116–124 (Jan. 18, 1989).
Grinius et al. "A Staphylococcal Multidrug Resistance Gene Product is a Member of a New Protein Family", *Plasmid* 27: 119–129 (1992).
Hamada et al. "Functional Role for the 170–to 180–kDa Glycoprotein Specific to Drug–Resistant Tumor Cells As Revealed By Monoclonal Antibodies", *Proc. Natl. Acad. Sci. USA* 83: 7785–7789 (Oct. 1986).
Iwahashi et al. "Specific Targeting and Killing Activities of Anti–P–Glycoprotein Monoclonal Antibody MRK 16 Directed Against Intrinsically Multidrug–Resistant Human Colorectal Carcinoma Cell Lines in the Nude Mouse Model", *Cancer Research* 53: 5475–5482 (Nov. 15, 1993).
Neyfakh et al. "Efflux–Mediated Multidrug Resistance in Bacillus Subtilis: Similarities and Dissimilarities With the Mammalian System", *Proc. Natl. Acad. Sci. USA* 88: 4781–4785 (Jun. 1991).
Noonan et al. "Quantitative Analysis of MDR1 (multidrug resistance) Gene Expression in Human Tumors By Polymerase Chain Reaction", *Proc. Natl. Acad. Sci. USA* 87: 7160–7164 (Sep. 1990).
Pearson et al. "Reversal of Drug Resistance in a Human Colon Cancer Xenograft Expressing MDR1 Complementary DNA by In Vivo Administration of MRK–16 Monoclonal Antibody", *J. Natl. Cancer Inst.* 83: 1386–1391 (1991).
Rittmann–Grauer et al. "Reversal of Vinca Alkaloid Resistance by Anti–Glycoprotein Monoclonal Antibody HYB–241 in a Human Tumor Xenograft", *Cancer Res.* 52: 1810–1816 (Apr. 1, 1992).

(List continued on next page.)

*Primary Examiner*—Frank C. Eisenschenk
*Attorney, Agent, or Firm*—Foley & Lardner

[57] ABSTRACT

Polyspecific immunoconjugates and antibody composites that bind a multidrug transporter protein and an antigen associated with a tumor or infectious agent are used to overcome the multidrug resistant phenotype. These immunoconjugates and composites also can be used diagnostically to determine whether the failure of traditional chemotherapy is due to the presence of multidrug resistant tumor cells, multidrug resistant HIV–infected cells or multidrug resistant infectious agents.

14 Claims, No Drawings

OTHER PUBLICATIONS

Sarkadi et al. "Interaction of Bioactive Hydrophobic Peptides With The Human Multidrug Transporter", *The FASEB Journal* 8: 766–770 (Jul. 1994).

Schneider et al. "P–Glycoprotein Expression in Treated and Untreated Human Breast Cancer", *Br. J. Cancer* 60: 815–818 (1989).

Sheldon et al. "Sensitivity of Multidrug Resistant KB–C1 Cells to an Antibody–Dextran–Adriamycin Conjugate", *Anticancer Research* 9: 637–642 (1989).

Tong et al. "Elimination of Chemoresistant Multiple Myeloma Clonogenic Colony–forming Cells by Combined Treatment with a Plasma Cell–reactive Monoclonal Antibody and a P–Glycoprotein–reactive Monoclonal Antibody" *Cancer Res.* 49: 4829–4834 (Sep. 1, 1989).

Van Diuk et al. "Bispecific Antibodies Reactive With The Multidrug–Resistance–Related Glycoprotein and CD3 Induce Lysis of Multidrug–Resistant Tumor Cells", *Int. J. Cancer* 44: 738–743 (1989).

Volm et al. "Detection of Multidrug Resistant Phenotype in Human Tumours by Monoclonal Antibodies and the Streptavidin–Biotinylated Phycoerythrin Complex Method", *Eur. J. Cancer Clin. Oncol.* 23:(4) 743–749 (1989).

POLYSPECIFIC IMMUNOCONJUGATES AND ANTIBODY COMPOSITES FOR TARGETING THE MULTIDRUG RESISTANT PHENOTYPE

BACKGROUND OF THE INVENTION

1. Field of the Invention

The present invention relates to novel polyspecific immunoconjugates that are useful for diagnosis and therapy of diseases caused by cells that are multidrug resistant. In particular, this invention relates to polyspecific immunoconjugates that comprise at least one moiety that binds with a multidrug transporter protein, at least one moiety that binds with a tumor associated antigen or infectious agent antigen, and a therapeutic or diagnostic agent. This invention also relates to methods of diagnosis and therapy using the polyspecific immunoconjugates. This invention further relates to diagnostic and therapeutic uses of antibody composites comprising at least one moiety that binds with a multidrug transporter protein, and at least one moiety that binds with a tumor associated antigen or infectious agent antigen.

2. Background

One of the major limitations of cancer chemotherapy is the development of drug resistance by cancer cells. Despite initial sensitivity to a particular chemotherapeutic agent, some tumors become progressively unresponsive to the particular agent, or to various chemotherapeutic agents. This phenomenon of acquired drug resistance is believed to be due to the selection and growth of drug resistant mutant tumor cells. See, for example, Deuchars et al., *Sem. Oncol.* 16: 156 (1989).

Cultured cell lines and transplantable tumors have been used to study the mechanism of acquired drug resistance in vitro. These studies have shown that under certain selection conditions, cells may acquire simultaneous resistance to a diverse group of drugs that are unrelated to the selecting agent in structure, cellular target and mode of action. See, for example, Bradley et al., *Biochim. Biophys. Acta* 948: 87 (1988); Deuchars et al., supra. Many of the drugs affected by this "multidrug-resistance" (MDR) phenotype are important in current treatment protocols, such as vincristine, actinomycin D, and adriamycin. Id.

The MDR phenotype is consistently associated with overexpression of a 170 kilodalton membrane glycoprotein, designated "gp170" or "P-glycoprotein." Endicott et al., *Ann. Rev. Biochem.* 58: 137 (1989); Kane et al., *J. Bioenerg. Biomembr.* 22: 593 (1990); Efferth et al., *Urol. Res.* 18: 309 (1990). Studies indicate that P-glycoprotein is a transmembrane protein responsible for an ATP-dependent efflux of a broad spectrum of structurally and functionally distinct drugs from multidrug-resistant cells. Riordan et al., *Pharmacol. Ther.* 28: 51 (1985). In fact, expression of P-glycoprotein has been shown to be predictive of a poor response to chemotherapy in a number of neoplasms. See, for example, Pearson et al., *J. Nat'l Cancer Inst.* 83: 1386 (1991).

Recent observations indicate that infectious agents can induce the MDR phenotype in noncancerous cells. For example, prolonged treatment with 3'-azido-3'-deoxythymidine (AZT) for human immunodeficiency virus (HIV) infection is associated with an acquired resistance to AZT. Gollapudi et al., *Biochem. Biophys. Res. Commun.* 171: 1002 (1990); Antonelli et al., *AIDS Research and Human Retroviruses* 8: 1839 (1992). In vitro studies demonstrate that HIV-infected human cells have an increased expression of P-glycoprotein and accumulate less AZT, compared with non-infected control cells. Id.; Gupta et al., *J. Clin. Immunol.* 13: 289 (1993). Thus, overexpression of P-glycoprotein and the accompanying MDR phenotype can impair chemotherapy with anti-viral drugs.

Considerable effort has been employed to overcome the multidrug-resistant phenotype and thus, improve the efficacy of chemotherapy. Most of these strategies have involved pharmacological agents that enhance the intracellular accumulation of the cancer drugs by biochemically inhibiting the multidrug transporter. See, for example, Ford et al., *Pharmacol. Rev.* 42: 155 (1990). Examples of agents that modulate P-glycoprotein activity include calcium channel blockers, calmodulin inhibitors, antiarrythmics, antimalarials, various lysoosmotropic agents, steroids, antiestrogens, and cyclic peptide antibiotics. Rittmann-Grauer et al., *Cancer Res.* 52: 1810 (1992).

However, multidrug-resistant reversing drugs used in early clinical trials have shown major side effects unrelated to the inhibition of P-glycoprotein, such as cardiac toxicity (verapamil) or immunosuppression (cyclosporin A), which limit the dosage of drug that can be administered. See, for example, Ozols et al., *J. Clin. Oncol.* 5: 641 (1987); Dalton et al., *J. Clin. Oncol.* 7: 415 (1989); Cano-Gauci et al., *Biochem. Pharmacol.* 36: 2115 (1987); Ford et al., supra. Thus, there has been limited success in reversing MDR in vivo due to the toxicity of many of these small modulators. See, for example, Rittmann-Grauer et al., supra.

The use of antibody-drug conjugates provides an alternative approach to overcoming the MDR phenotype. For example, in vitro studies have shown that MDR can be partially overcome by conjugating the resistant drug to an antitumor antibody to increase uptake and subsequent cell death. Durrant et al., *Brit. J. Cancer* 56: 722 (1987); Sheldon et al., *Anticancer Res.* 9: 637 (1989). This approach, however, lacks specificity for tumor cells that express the MDR phenotype.

A more targeted approach to overcoming the MDR phenotype is to use antibodies or antibody conjugates that bind with P-glycoprotein. For example, the administration of an anti-P-glycoprotein monoclonal antibody and a resistant drug can increase the survival time of nude mice that carry human tumor cells. Pearson et al., *J. Nat'l Cancer Inst.* 83: 1386 (1991); Iwahashi et al., *Cancer Res.* 53: 5475 (1993). Also, see Grauer et al., international publication No. WO 93/02105 (1993). In addition, an anti-P-glycoprotein monoclonal antibody-Pseudomonas toxin conjugate has been shown to kill multidrug-resistant human cells in vitro. FitzGerald et al., *Proc. Nat'l Acad. Sci. USA* 84: 4288 (1987). Also, see Efferth et al., *Med. Oncol. & Tumor Pharmacother.* 9: 11 (1992), and Mechetner et al., international publication No. WO 93/19094 (1993).

Similarly, investigators have produced bispecific antibodies comprising a P-glycoprotein binding moiety and a moiety that binds with a cytotoxic cell. van Dijk et al., *Int. J. Cancer* 44: 738 (1989); Ring et al., international Publication No. WO 92/08802 (1992). The theory behind this approach is that the bispecific antibodies can be used to direct cytotoxic cells to multidrug-resistant cells that express P-glycoprotein.

However, studies have shown that P-glycoprotein is expressed in normal human tissues, such as liver, kidney, adrenal gland, pancreas, colon and jejunum. See, for example, Endicott et al., *Ann. Rev. Biochem.* 58: 137 (1989). Consequently, investigators have warned that "blocking P-glycoprotein action in order to circumvent MDR will also affect the normally expressed P-glycoprotein and this may cause unacceptable side toxic effects." Childs et al., "The MDR Superfamily of Genes and Its Biological Implications," in IMPORTANT ADVANCES IN ONCOLOGY 1994, DeVita et al., (eds.), pages 21–36 (J. B. Lippincott Co. 1994). This admonition particularly applies to therapeutic methods that use antibody conjugates consisting of a P-glycoprotein binding moiety and a cytotoxic agent. Therefore, the success of an antibody-directed treatment of MDR tumors will mainly depend upon the ability to kill drug-resistant tumor cells with tolerable side effects to normal tissues of the patient. Efferth et al., Med. Oncol. & Tumor Pharmacother. 9: 11 (1992).

Thus, an need exists for a method to overcome the MDR phenotype but that also minimizes toxicity to normal tissue.

The emergence of the MDR phenotype also is the major cause of failure in the treatment of infectious diseases. Davies, Science 264: 375 (1994). In particular, pathogenic bacteria have active drug efflux systems of very broad substrate specificity. Nikaido, Science 264: 382 (1994), which is incorporated by reference. For example, studies indicate that a drug efflux system plays a major role in the intrinsic resistance of Psuedomonas aeruginosa, a common opportunistic pathogen. Poole et al., Mol. Microbiol. 10: 529 (1993); Poole et al., J. Bacteriol. 175: 7363 (1993).

Recent studies indicate that bacterial drug efflux systems are functionally similar to the mammalian MDR efflux pump. As an illustration, both the Bacillus subtilis and the mammalian multidrug transporters can be inhibited by reserpine and verapamil. Neyfakh et al., Proc. Nat'l Acad. Sci. 88: 4781 (1991). Moreover, investigators have recognized a superfamily of ATP-dependent membrane transporters that includes prokaryotic permeases and mammalian P-glycoprotein. Doige et al., Ann. Rev. Microbiol. 47: 291 (1993).

Active drug efflux as a mechanism for drug resistance is significant in nonbacterial infectious agents. For instance, a Plasmodium falciparum protein is involved in imparting resistance to quinoline-containing drugs used for prophylaxis and treatment of malaria. Id.; Bray, FEMS Microbiol. Lett. 113: 1 (1993). In addition, drug resistance has been linked to active efflux in the fungus, Aspergillus nidulans. de Waard et al., Pestic. Biochem. Physiol. 13: 255 (1980).

Historically, the pharmaceutical industry has concentrated on designing drugs to overcome specific mechanisms of MDR in infectious agents, such as increased degradation of particular drugs and inactivation of drugs by enzymatic modification of specific groups. Nikaido et al., supra. However, in the future, general mechanisms of MDR, such as active drug efflux, are likely to become more important in the clinical setting.

Thus, a need exists for methods that can be used to inhibit the function of multidrug transporter proteins expressed by infectious agents.

SUMMARY OF THE INVENTION

Accordingly, it is an object of the present invention to provide a method for overcoming the multidrug-resistant phenotype that has a therapeutic index superior to conventional methods.

Another object of this invention is to provide methods for selectively targeting diagnostic and therapeutic agents to multidrug-resistant cells, while avoiding major toxic side effects to normal organs.

Another object of this invention is to provide antibody composites that bind a multidrug transporter protein and an antigen associated with a tumor or infectious agent.

A further object of this invention is to provide polyspecific immunoconjugates which are conjugates of antibody composites and diagnostic or therapeutic agents.

These and other objects are achieved, in accordance with one embodiment of the present invention by the provision of a polyspecific immunoconjugate comprising:

(a) at least one antibody component that binds with a first epitope of a multidrug transporter protein;

(b) at least one antibody component that binds with a first epitope of an antigen, wherein the antigen is associated with a tumor or an infectious agent; and (c) at least one diagnostic or therapeutic agent.

The antibody components of such a polyspecific immunoconjugate are selected from the group consisting of (a) a murine monoclonal antibody; (b) a humanized antibody derived from (a); (c) a human monoclonal antibody; (d) a subhuman primate antibody; and (e) an antibody fragment derived from (a), (b), (c) or (d), wherein the antibody fragment is selected from the group consisting of $F(ab')_2$, $F(ab)_2$, Fab', Fab, Fv, sFv and minimal recognition unit. The multidrug transporter protein of such a polyspecific immunoconjugate is selected from the group consisting of P-glycoprotein, OtrB, Tel(L), Mmr, ActII, TcmA, NorA, QacA, CmlA, Bcr, EmrB, EmrD, AcrE, EnvD, MexB, Smr, QacE, MvrC, MsrA, DrrA, DrrB, TlrC, Bmr, TetA and OprK.

As stated above, the polyspecific immunoconjugate comprises a diagnostic or therapeutic agent. A suitable diagnostic agent is selected from the group consisting of radioactive label, photoactive agent or dye, florescent label, enzyme label, bioluminescent label, chemiluminescent label, colloidal gold and paramagnetic ion. Moreover, a suitable radioactive label may be a γ-emitter or a positron-emitter. Preferably, γ-emitters have a gamma radiation emission peak in the range of 50–500 Kev, such as a radioisotope selected from the group consisting of $^{99m}$Tc, $^{67}$Ga, $^{123}$I and $^{131}$I.

A suitable therapeutic agent is selected from the group consisting of radioisotope, boron addend, immunomodulator, toxin, photoactive agent or dye, cancer chemotherapeutic drug, antiviral drug, antifungal drug, antibacterial drug, antiprotozoal drug and chemosensitizing agent. Moreover a suitable therapeutic radioisotope is selected from the group consisting of α-emitters, β-emitters, γ-emitters, Auger electron emitters, neutron capturing agents that emit α-particles and radioisotopes that decay by electron capture. Preferably, the radioisotope is selected from the group consisting of $^{198}$Au, $^{32}$P, $^{125}$I, $^{131}$I, $^{90}$Y, $^{186}$Re, $^{67}$Cu and $^{211}$At.

The present invention also contemplates polyspecific immunoconjugates which further comprise an antibody component that binds with a second epitope of the multidrug transporter protein. Moreover, polyspecific immunoconjugates may additionally comprise an antibody component that binds with a second epitope of the tumor or infectious agent associated antigen, or with an epitope of a second antigen associated with the tumor or the infectious agent.

The present invention also is directed to a method for treating a mammal having either a multidrug resistant tumor that expresses a tumor associated antigen or a multidrug resistant disease caused by an infectious agent, the method comprising the step of administering a polyspecific immunoconjugate to the mammal, wherein the polyspecific immunoconjugate comprises:

(a) at least one antibody component that binds with a first epitope of a multidrug transporter protein, (b) at least one antibody component that binds with a first epitope of an antigen, wherein the antigen is associated with the tumor or the infectious agent, and (c) at least one therapeutic agent.

Moreover, the present invention contemplates methods further comprising the administration of a chemosensitizing agent or immunomodulator to the mammal.

In addition, the present invention is directed to a method for detecting the location of multidrug resistant (MDR) tumor cells, MDR HIV-infected cells or MDR infectious agents in a mammal having a multidrug resistant disease caused by a tumor or infectious agent, the method comprising the steps of:

(a) parenterally injecting the mammal with an antibody composite comprising (1) at least one antibody component that binds a first epitope of a multidrug transporter protein, and (2) at least one antibody component that binds a first epitope of an antigen that is associated with the tumor or the infectious agent, wherein the antibody composite is conjugated with a biotin-binding molecule or with biotin;

(b) parenterally injecting a clearing composition comprised of:
  (i) biotin, when the antibody composite is conjugated with a biotin-binding molecule, or
  (ii) a biotin-binding molecule, when the antibody composite is conjugated with biotin,
  and allowing the clearing composition to substantially clear the antibody composite from sites that do not contain MDR tumor cells, MDR HIV-infected cells or MDR infectious agents; and (c) parenterally injecting a diagnostic composition comprised of:
  (i) biotin, when the antibody composite is conjugated with a biotin-binding molecule, or
  (ii) a biotin-binding molecule, when the antibody composite is conjugated with biotin,
  and a diagnostic agent which is conjugated with the biotin or the biotin-binding molecule.

In such a detection method, the diagnostic agent is selected from the group consisting of radioactive label, photoactive agent or dye, fluorescent label and paramagnetic ion. Moreover, the biotin-binding molecule is avidin or streptavidin.

The present invention also contemplates a method for treating a mammal having a multidrug resistant disease caused by a tumor or infectious agent, the method comprising the steps of:

(a) parenterally injecting the mammal with an antibody composite comprising (1) at least one antibody component that binds a first epitope of a multidrug transporter protein, and (2) at least one antibody component that binds a first epitope of an antigen that is associated with the tumor or the infectious agent, wherein the antibody composite is conjugated with a biotin-binding molecule or with biotin;

(b) parenterally injecting a clearing composition comprised of:
  (i) biotin, when the antibody composite is conjugated with a biotin-binding molecule, or
  (ii) a biotin-binding molecule, when the antibody composite is conjugated with biotin,
  and allowing the clearing composition to substantially clear the antibody composite from sites that do not contain multidrug resistant (MDR) cells or MDR infectious agents; and (c) parenterally injecting a therapeutic composition comprised of:
  (i) biotin, when the antibody composite is conjugated with a biotin-binding molecule, or
  (ii) a biotin-binding molecule, when the antibody composite is conjugated with biotin,
  and a therapeutic agent which is conjugated with the biotin or the biotin-binding molecule.

A suitable therapeutic agent is selected from the group consisting of radioisotope, boron addend, toxin, immunomodulator, photoactive agent or dye, cancer chemotherapeutic drug, antiviral drug, antifungal drug, antibacterial drug, antiprotozoal drug and a chemosensitizing agent. Again, the biotin-binding molecule is avidin or streptavidin.

The present invention also is directed to a method for detecting the presence of multidrug resistant (MDR) tumor cells, MDR HIV-infected cells or MDR infectious agents in a mammal, the method comprising:

(a) removing from the mammal a biological sample that is suspected of containing MDR tumor cells, MDR HIV-infected cells or MDR infectious agents;

(b) contacting the biological sample with an antibody composite which comprises (1) at least one antibody component that binds with a first epitope of a multidrug transporter protein, and (2) at least one antibody component that binds with a first epitope of an antigen that is associated with the tumor or the infectious agent, wherein the contacting is performed under conditions which allow the binding of the antibody composite to the biological sample; and (c) detecting any of the bound antibody composite.

Here, a suitable diagnostic agent selected from the group consisting of radioisotope, fluorescent label, chemiluminescent label, enzyme label, bioluminescent label and colloidal gold. Moreover, the antibody composite can further comprise biotin or a biotin-binding molecule.

The present invention is further directed to a method for detecting the location of multidrug resistant (MDR) tumor cells, MDR HIV-infected cells or MDR infectious agents in a mammal having a multidrug resistant disease caused by a tumor or infectious agent, the method comprising the steps of:

(a) parenterally injecting the mammal with a polyspecific immunoconjugate that comprises (1) at least one antibody component that binds with a first epitope of a multidrug transporter protein, (2) at least one antibody component that binds with a first epitope of an antigen that is associated with the tumor or infectious agent, and (3) a diagnostic agent;

(b) parenterally injecting the mammal with an antibody or antibody fragment that binds with the polyspecific immunoconjugate in an amount that is sufficient to decrease the level of circulating polyspecific immunoconjugate by about 10–85% within 2 to 72 hours;

(c) scanning the mammal with a detector to locate the site or sites of uptake of the polyspecific immunoconjugate.

A suitable diagnostic agent is selected from the group consisting of radioactive label, photoactive agent or dye, fluorescent label and paramagnetic ion.

The present invention also contemplates a method for treating a mammal having a multidrug resistant disease caused by a tumor or infectious agent, the method comprising the steps of:

(a) parenterally injecting the mammal with a polyspecific immunoconjugate comprising (1) at least one antibody component that binds with a first epitope of a multidrug transporter protein, (2) at least one antibody component that binds with a first epitope of an antigen that is associated with the tumor or infectious agent, and (3) a therapeutic agent; and (b) parenterally injecting the mammal with an antibody or antibody fragment that binds with the polyspecific immunoconjugate in an amount that is sufficient to decrease the level of circulating polyspecific immunoconjugate by about 10–85% within 2 to 72 hours.

In addition, the present invention is directed to a method for detecting the location of multidrug resistant (MDR) tumor cells, MDR HIV-infected cells or MDR infectious agents in a subject having a multidrug resistant disease caused by a tumor or infectious agent, the method comprising the steps of:

(a) parenterally injecting the subject with a polyspecific immunoconjugate comprising (1) at least one antibody component that binds with a first epitope of a multidrug transporter protein, (2) at least one antibody component that binds with a first epitope of an antigen that is associated with a tumor or infectious agent, and (3) a diagnostic agent;

(b) surgically exposing or endoscopically accessing the interior of the body cavity of the subject; and (c) scanning the interior body cavity with a detection probe to detect the sites of accretion of the polyspecific immunoconjugate.

Suitable diagnostic agents include radioisotopes, such as a γ-emitter or a positron-emitter, and a photoactive agent or dye that is detected by laser-induced fluorescence.

The present invention also contemplates a method for treating a subject having a multidrug resistant disease caused by a tumor or infectious agent, the method comprising the steps of:

(a) parenterally injecting the subject with a polyspecific immunoconjugate comprising (1) at least one antibody component that binds with a first epitope of a multidrug transporter protein, (2) at least one antibody component that binds with a first epitope of an antigen that is associated with a tumor or infectious agent, and (3) a photoactive agent or dye;

(b) surgically exposing or endoscopically accessing the interior of the body cavity of the subject; and (c) treating sites of accretion of the polyspecific immunoconjugate to light, wherein the treatment activates the photoactive agent or dye.

In addition, the present invention is directed to an antibody composite comprising:

(a) at least one antibody component that binds with a first epitope of a multidrug transporter protein; and (b) at least one antibody component that binds with a first epitope of an antigen, wherein the antigen is associated with a tumor or an infectious agent.

Suitable antibody components of antibody composites are selected from the group consisting of (a) a murine monoclonal antibody; (b) a humanized antibody derived from (a); (c) a human monoclonal antibody; (d) a subhuman primate antibody; and (e) an antibody fragment derived from (a), (b), (c) or (d), where an antibody fragment is selected from the group consisting of F(ab')$_2$, F(ab)$_2$, Fab', Fab, Fv, sFv and minimal recognition unit. Moreover, a suitable multidrug transporter protein is selected from the group consisting of P-glycoprotein, OtrB, Tel(L), Mmr, ActII, TcmA, NorA, QacA, CmlA, Bcr, EmrB, EmrD, AcrE, EnvD, MexB, Smr, QacE, MvrC, MsrA, DrrA, DrrB, TlrC, Bmr, TetA and OprK.

The present invention also contemplates an antibody composite further comprising an antibody component that binds with a second epitope of the multidrug transporter protein. An antibody composite can additionally include an antibody component that binds with a second epitope of the tumor or infectious agent associated antigen, or with an epitope of a second antigen associated with the tumor or the infectious agent.

The present invention is further directed to a method for treating a mammal having either a multidrug resistant tumor that expresses a tumor associated antigen or a multidrug resistant disease caused by an infectious agent, the method comprising the step of administering an antibody composite to the mammal, wherein the antibody composite comprises:

(a) at least one antibody component that binds with a first epitope of a multidrug transporter protein, and (b) at least one antibody component that binds with a first epitope of an antigen, wherein the antigen is associated with the tumor or the infectious agent.

Moreover, the present invention contemplates a method further comprising the step of administering a therapeutic agent to the mammal, wherein the therapeutic agent is selected from the group consisting of cancer chemotherapeutic drug, antiviral drug, antifungal drug, antibacterial drug and antiprotozoal drug. Finally, the present invention also is directed to a method which further comprises the step of administering an immunomodulator, wherein the immunomodulator is selected from the group consisting of cytokine, stem cell growth factor and hematopoietic factor.

DETAILED DESCRIPTION

1. Definitions

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned T cell receptor gene is a DNA fragment that has been separated from the genomic DNA of a mammalian cell. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A tumor associated antigen is a protein normally not expressed, or expressed at very low levels, by a normal counterpart. Examples of tumor associated antigens include α-fetoprotein and carcinoembryonic antigen (CEA). Many other illustrations of tumor associated antigens are known to those of skill in the art. See, for example, Urban et al., *Ann. Rev. Immunol.* 10: 617 (1992).

As used herein, an infectious agent denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to antibody-induced clearance or lytic or phagocytic destruction, such as malarial parasites, spirochetes, and the like.

A multidrug transporter protein is a membrane-associated protein which transports diverse cytotoxic compounds out of a cell in an energy-dependent manner. Examples of multidrug transporter proteins include P-glycoprotein, OtrB, Tel (L), Mmr, ActII, TcmA, NorA, QacA, CmlA, Bcr, EmrB, EmrD, AcrE, EnvD, MexB, Smr, QacE, MvrC, MsrA, DrrA, DrrB, TlrC, Bmr, TetA, OprK, and the like.

An antibody fragment is a portion of an antibody such as F(ab')₂, F(ab)₂, Fab', Fab, and the like. Regardless of structure, an antibody fragment binds with the same antigen that is recognized by the intact antibody.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

Humanized antibodies are recombinant proteins in which murine complementary determining regions of monoclonal antibodies have been transferred from heavy and light variable chains of the murine immunoglobulin into a human variable domain.

As used herein, the term antibody component includes both an entire antibody and an antibody fragment.

As used herein, a diagnostic or therapeutic agent is a molecule or atom which is conjugated to an antibody moiety to produce a conjugate which is useful for diagnosis or for therapy. Examples of diagnostic or therapeutic agents include drugs, toxins, immunomodulators, chelators, boron compounds, photoactive agents or dyes, radioisotopes, fluorescent agents, paramagnetic ions or molecules and marker moieties.

An antibody composite is a polyspecific antibody composition comprising at least two substantially monospecific antibody components, wherein at least one antibody component binds with an epitope of a multidrug transporter protein, and wherein at least one antibody component binds with an antigen that is associated with either a tumor or an infectious agent.

A polyspecific immunoconjugate is a conjugate of an antibody composite with a diagnostic or therapeutic agent.

2. Production of Rodent Monoclonal Antibodies, Humanized Antibodies, Primate Antibodies and Human Antibodies An antibody composite of the present invention may be derived from a rodent monoclonal antibody (MAb). Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in METHODS IN MOLECULAR BIOLOGY, VOL. 10, pages 79–104 (The Humana Press, Inc. 1992).

A wide variety of monoclonal antibodies against tumor associated antigens or infectious agents have been developed. See, for example, Goldenberg et al., international application publication No. WO 91/11465 (1991), Hansen et al., international application publication No. WO 93/23062, and Goldenberg, international application publication No. WO 94/04702 (1994), each of which is incorporated by reference in its entirety.

Furthermore, such antibodies are readily available from commercial sources. For example, rodent monoclonal antibodies that bind with adenocarcinoma-associated antigen (Cat. No. 121730), human chorionic gonadotropin (Cat. No. 230740), carcinoembryonic antigen (Cat. Nos. 215920 and 215922), human alpha-fetoprotein (Cat. No. 341646), and the like can be obtained from Calbiochem-Novabiochem Corp. (San Diego, Calif.). Moreover, rodent monoclonal antibodies that bind with antigenic determinants of infectious agents such as *Escherichia coli* (HB 8178), *Legionella pneumophila* (CRL 1770), *Schistosoma mansoni* (HB 8088), Streptococcus, Group A (HB 9696), *Treponema pallidum*

(HB 8134), hepatitis B (CRL 8017), herpes simplex (HB 8181), human immunodeficiency virus (HB 9101), among others, can be obtained from American Type Culture Collection (Rockville, Md.). Furthermore, murine monoclonal antibodies against merozoites and sporozoites of *Plasmodium falciparum* can be prepared as described by Goldenberg, U.S. Pat. No. 5,332,567 (1994), which is incorporated by reference.

Methods for producing P-glycoprotein antibodies are well-known to those of skill in the art. See, for example, Lathan et al., *Cancer Res.* 45: 5064 (1985); Kartner et al., *Nature* 316: 820 (1985); Hamada et al., *Proc. Nat'l Acad. Sci* 83: 7785 (1986); Scheper et al., *Int. J. Cancer* 42: 389 (1988); Rittmann-Grauer et al., *Cancer Res.* 52: 1810 (1992); Ling et al., U.S. Pat. No. 4,837,306 (1989); Ring et al., international publication No. WO 92/08802; Grauer et al., international publication No. WO 93/02105; and Mechetner et al., international publication No. WO 93/19094, which are incorporated by reference. Since P-glycoprotein retains its structural identity across different mammalian species (Rubin, U.S. Pat. No. 5,005,588; Kane et al., *J. Bioenergetics and Biomembranes* 22: 593 (1990)), antibodies raised against P-glycoprotein from non-human cells can be used for diagnosis and therapy in humans. Conversely, antibodies raised against human P-glycoprotein should be suitable for veterinary uses.

Preferred P-glycoprotein antibodies bind with the extracellular domain of P-glycoprotein, and can be produced against cells that express the MDR phenotype as described, for example, by Mechetner et al., supra, and Rittmann-Grauer et al., supra. Alternatively, such antibodies can be obtained using peptides that contain an extracellular epitope P-glycoprotein. See, for example, Cianfriglia et al., international publication No. WO 93/25700, which is incorporated by reference.

Those of skill in the art can readily apply standard techniques to produce antibodies against multidrug transporter proteins of infectious agents. Suitable antigens include multidrug transporter proteins such as Bmr, TetA, EmrB, OprK, Smr, and the like. See, for example, Nikaido et al., supra; Poole et al., *J. Bacteriol.* 175: 7363 (1993); and Childs et al., "The MDR Superfamily of Genes and Its Biological Implications," in IMPORTANT ADVANCES IN ONCOLOGY 1994, DeVita et al., (eds.), pages 21–36 (J. B. Lippincott Co. 1994), which are incorporated by reference. One approach for preparing antibodies against infectious agent multidrug transporter proteins is illustrated in Example 6.

An antibody composite of the present invention may also be derived from a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46: 310 (1990), which is incorporated by reference.

Alternatively, an antibody composite may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

As an alternative, an antibody composite of the present invention may be derived from human antibody fragments isolated from a combinatorial immunoglobulin library. See, for example, Barbas et al., *METHODS: A Companion to Methods in Enzymology* 2: 119 (1991), and Winter et al., *Ann. Rev. Immunol.* 12: 433 (1994), which are incorporated by reference. Cloning and expression vectors that are useful for producing a human immunoglobulin phage library can be obtained, for example, from STRATAGENE Cloning Systems (La Jolla, Calif.).

In addition, an antibody composite of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7: 13 (1994), Lonberg et al., *Nature* 368: 856 (1994), and Taylor et al., *Int. Immun.* 6: 579 (1994), which are incorporated by reference.

3. Production of Antibody Fragments

The present invention contemplates the use of antibody fragments to produce antibody composites. Antibody fragments can be prepared by proteolytic hydrolysis of the antibody or by expression in *E. coli* of the DNA coding for the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69: 2659 (1972). Alternatively, the variable chains can be linked by an intermolecular disulfide bond or crosslinked by chemicals such as glutaraldehyde. See, for example, Sandhu, supra.

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2: 97 (1991). Also see Bird et al., *Science* 242:423–426 (1988), Ladner et al., U.S. Pat. No. 4,946,778, Pack et al., *Bio/Technology* 11:1271–1277 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991).

4. Production of Antibody Composites

Antibody composites can be prepared by a variety of conventional procedures, ranging from glutaraldehyde linkage to more specific linkages between functional groups. The antibodies and/or antibody fragments are preferably covalently bound to one another, directly or through a linker moiety, through one or more functional groups on the antibody or fragment, e.g., amine, carboxyl, phenyl, thiol, or hydroxyl groups. Various conventional linkers in addition to glutaraldehyde can be used, e.g., disiocyanates, diiosothiocyanates, bis(hydroxysuccinimide) esters, carbodiimides, maleimidehydroxysuccinimde esters, and the like. The optimal length of the linker may vary according to the type of target cell. The most efficacious linker size can be determined by using antibody composites with various linker lengths for the immunochemical staining of a patient tissue sample that contains cells expressing a multidrug transporter protein and the target antigen. Immunochemical techniques are described below.

A simple method to produce antibody composites is to mix the antibodies or fragments in the presence of glutaraldehyde to form an antibody composite. The initial Schiff base linkages can be stabilized, e.g., by borohydride reduction to secondary amines. A diiosothiocyanate or carbodiimide can be used in place of glutaraldehyde as a non-site-specific linker.

The simplest form of an antibody composite is a bispecific antibody comprising binding moieties for a multidrug transporter protein and an antigen that is associated with a tumor cell or infectious agent. Bispecific antibodies can be made by a variety of conventional methods, e.g., disulfide cleavage and reformation of mixtures of whole IgG or, preferably F(ab')₂ fragments, fusions of more than one hybridoma to form polyomas that produce antibodies having more than one specificity, and by genetic engineering. Bispecific antibody composites have been prepared by oxidative cleavage of Fab' fragments resulting from reductive cleavage of different antibodies. This is advantageously carried out by mixing two different F(ab')₂ fragments produced by pepsin digestion of two different antibodies, reductive cleavage to form a mixture of Fab' fragments, followed by oxidative reformation of the disulfide linkages to produce a mixture of F(ab')₂ fragments including bispecific antibody composites containing a Fab' potion specific to each of the original epitopes. General techniques for the preparation of antibody composites may be found, for example, in Nisonhoff et al., *Arch Biochem. Biophys.* 93: 470 (1961), Hammerling et al., *J. Exp. Med.* 128: 1461 (1968), and U.S. Pat. No. 4,331,647.

More selective linkage can be achieved by using a heterobifunctional linker such as maleimide-hydroxysuccinimide ester. Reaction of the ester with an antibody or fragment will derivatize amine groups on the antibody or fragment, and the derivative can then be reacted with, e.g., an antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfydryl groups, as noted above. Another method involves reacting an antibody having an oxidized carbohydrate portion with another antibody which has at lease one free amine function. This results in an initial Schiff base (imine) linkage, which is preferably stabilized by reduction to a secondary amine, e.g., by borohydride reduction, to form the final composite. Such site-specific linkages are disclosed, for small molecules, in U.S. Pat. No. 4,671,958, and for larger addends in U.S. Pat. No. 4,699,784.

In the present context, a bispecific antibody comprises binding moieties for a multidrug transporter protein and an antigen that is associated with a tumor cell or infectious agent. For example, the multidrug transporter protein-binding moiety can be derived from anti-multidrug transporter protein Mab, while a carcinoembryonic antigen (CEA) binding moiety can be derived from a Class III Mab. Methods for preparing multidrug transporter protein Mab are described above, while methods for preparing Class III anti-CEA Mab are described by Primus et al., *Cancer Research* 43: 686 (1983), and by Primus et al., U.S. Pat. No. 4,818,709, which are incorporated by reference.

For example, a bispecific antibody can be prepared by obtaining an F(ab')₂ fragment from an anti-CEA Class III Mab, using the techniques described above. The interchain disulfide bridges of the anti-CEA Class III F(ab')₂ fragment are gently reduced with cysteine, taking care to avoid light-heavy chain linkage, to form Fab'-SH fragments. The SH group(s) is(are) activated with an excess of bis-maleimide linker (1,1'-(methylenedi-4,1-phenylene)bis-malemide). The multidrug transporter protein Mab is converted to Fab'-SH and then reacted with the activated anti-CEA Class III Fab'-SH fragment to obtain a bispecific antibody.

Alternatively, such bispecific antibodies can be produced by fusing two hybridoma cell lines that produce anti-multidrug transporter protein Mab and anti-CEA Class III Mab. Techniques for producing tetradomas are described, for example, by Milstein et al., *Nature* 305: 537 (1983) and Pohl et al., *Int. J. Cancer* 54: 418 (1993).

Finally, such bispecific antibodies can be produced by genetic engineering. For example, plasmids containing DNA coding for variable domains of an anti-CEA Class III Mab can be introduced into hybridomas that secrete anti-multidrug transporter protein antibodies. The resulting "transfectomas" produce bispecific antibodies that bind CEA and the multidrug transporter protein. Alternatively, chimeric genes can be designed that encode both anti-multidrug transporter protein and anti-CEA binding domains. General techniques for producing bispecific antibodies by genetic engineering are described, for example, by Songsivilai et al., *Biochem. Biophys. Res. Commun.* 164: 271 (1989); Traunecker et al., *EMBO J.* 10: 3655 (1991); and Weiner et al., *J. Immunol.* 147: 4035 (1991).

A polyspecific antibody composite can be obtained by adding various antibody components to a bispecific antibody composite. For example, a bispecific antibody can be reacted with 2-iminothiolane to introduce one or more sulfhydryl groups for use in coupling the bispecific antibody to an antibody component that binds an epitope of a multidrug transporter protein that is distinct from the epitope bound by the bispecific antibody, using the bis-maleimide activation procedure described above. These techniques for producing antibody composites are well known to those of skill in the art. See, for example, U.S. Pat. No. 4,925,648, and Goldenberg, international publication No. WO 92/19273, which are incorporated by reference.

5. Preparation of Polyspecific Immunoconjugates

Polyspecific immunoconjugates can be prepared by indirectly conjugating a diagnostic or therapeutic agent to an antibody composite. General techniques are described in Shih et al., *Int. J. Cancer* 41:832–839 (1988); Shih et al., *Int. J. Cancer* 46:1101–1106 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, boron addends, or other diagnostic or therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final polyspecific immunoconjugate is soluble in an aqueous solution, such as mammalian serum, for ease of administration and effective targeting for use in diagnosis or therapy. Thus, solubilizing functions on the carrier polymer will enhance the serum solubility of the final polyspecific immunoconjugate. Solubilizing functions also are important for use of polyspecific immunoconjugates for immunochemical detection, as described below. In particular, an aminodextran will be preferred.

The process for preparing a polyspecific immunoconjugate with an aminodextran carrier typically begins with a dextran polymer, advantageously a dextran of average molecular weight of about 10,000–100,000. The dextran is reacted with an oxidizing agent to effect a controlled oxidation of a portion of its carbohydrate rings to generate aldehyde groups. The oxidation is conveniently effected with glycolytic chemical reagents such as $NaIO_4$, according to conventional procedures.

The oxidized dextran is then reacted with a polyamine, preferably a diamine, and more preferably, a mono- or polyhydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to insure substantially complete conversion of the aldehyde functions to Schiff base groups.

A reducing agent, such as $NaBH_4$, $NaBH_3CN$ or the like, is used to effect reductive stabilization of the resultant Schiff base intermediate. The resultant adduct can be purified by passage through a conventional sizing column to remove cross-linked dextrans.

Other conventional methods of derivatizing a dextran to introduce amine functions can also be used, e.g., reaction with cyanogen bromide, followed by reaction with a diamine.

The aminodextran is then reacted with a derivative of the particular drug, toxin, chelator, paramagnetic ion, boron addend, or other diagnostic or therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as pokeweed antiviral protein or ricin A-chain, and the like, can be coupled to aminodextran by glutaraldehyde condensation or by reaction of activated carboxyl groups on the protein with amines on the aminodextran.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Labels such as enzymes, fluorescent compounds, electron transfer agents, and the like can be linked to a carrier by conventional methods well known to the art. These labeled carriers and the polyspecific immunoconjugates prepared from them can be used for immunochemical detection, as described below.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful polyspecific immunoconjugates, as described below.

A polypeptide carrier can be used instead of aminodextran, but the polypeptide carrier must have at least 50 amino acid residues in the chain, preferably 100–5000 amino acid residues. At least some of the amino acids should be lysine residues or glutamate or aspartate residues. The pendant amines of lysine residues and pendant carboxylates of glutamine and aspartate are convenient for attaching a drug, toxin, chelator, boron addend or other diagnostic or therapeutic agent. Examples of suitable polypeptide carriers include polylysine, polyglutamic acid, polyaspartic acid, copolymers thereof, and mixed polymers of these amino acids and others, e.g., serines, to confer desirable solubility properties on the resultant loaded carrier and polyspecific immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, boron addend, or other diagnostic or therapeutic agent.

Alternatively, an intermediate conjugate can be attached to an oxidized antibody component via amine groups that have been introduced in the intermediate conjugate after loading with the diagnostic or therapeutic agent. Oxidation is conveniently effected either chemically, e.g., with NaIO$_4$ or other glycolytic reagent, or enzymatically, e.g., with neuraminidase and galactose oxidase. In the case of an aminodextran carrier, not all of the amines of the aminodextran are typically used for loading a diagnostic or therapeutic agent. The remaining amines of aminodextran condense with the oxidized antibody component to form Schiff base adducts, which are then reductively stabilized, normally with a borohydride reducing agent.

Analogous procedures are used to produce other polyspecific immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final polyspecific immunoconjugate is purified using conventional techniques, such as sizing chromatography on Sephacryl S-300.

Alternatively, polyspecific immunoconjugates can be prepared by directly conjugating an antibody component with a diagnostic or therapeutic agent. The general procedure is analogous to the indirect method of conjugation except that a diagnostic or therapeutic agent is directly attached to an oxidized antibody component.

It will be appreciated that other diagnostic or therapeutic agents can be substituted for the chelators described herein. Those of skill in the art will be able to devise conjugation schemes without undue experimentation.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching a diagnostic or therapeutic agent to a carbohydrate moiety and to a free sulfhydryl group. Such a free sulfhydryl group may be located in the hinge region of the antibody component.

6. Use of Polyspecific Immunoconjugates Antibody Composites for Diagnosis

In Vitro Diagnosis

The present invention contemplates the use of polyspecific immunoconjugates and antibody composites to screen biological samples in vitro for the expression of P-glycoprotein by tumor cells. For example, the polyspecific immunoconjugates and antibody composites of the present invention can be used to detect the presence of P-glycoprotein and tumor associated antigen in tissue sections prepared from a biopsy specimen. Such immunochemical detection can be used to determine the abundance of P-glycoprotein and to determine the distribution of P-glycoprotein in the examined tissue. General immunochemistry techniques are well-known to those of ordinary skill. See, for example, Ponder, "Cell Marking Techniques and Their Application," in MAMMALIAN DEVELOPMENT: A PRACTICAL APPROACH, Monk (ed.), pages 115–38 (IRL Press 1987), Volm et al., *Eur. J. Cancer Clin. Oncol.* 25: 743 (1989), Coligan at pages 5.8.1–5.8.8, and Ausubel et al. (eds.), CURRENT PROTOCOLS IN MOLECULAR BIOLOGY, pages 14.6.1 to 14.6.13 (Wiley Interscience 1990). Also, see generally, Manson (ed.), METHODS IN MOLECULAR BIOLOGY, VOL. 10: IMMUNOCHEMICAL PROTOCOLS (The Humana Press, Inc. 1992). Moreover, methods for the immunochemical detection of P-glycoprotein are described, for example, by Dalton et al., *Blood* 73: 747 (1989), and Volm et al., *Eur. J. Cancer Clin. Oncol.* 25: 743 (1989).

In addition, the present invention contemplates the use of polyspecific immunoconjugates and antibody composites to screen biological samples in vitro for the expression of a multidrug transporter protein by an infectious agent. For example, the polyspecific immunoconjugates and antibody composites of the present invention can be used to detect the presence of OprK protein in clinical isolates. The presence of this particular multidrug transporter protein would indicate that the tissue was infected with multidrug resistant *Psuedomonas aeruginosa*.

Moreover, immunochemical detection techniques can be used to optimize antibody composites for subsequent in vivo diagnosis and therapy in the form of antibody composites per se or as polyspecific immunoconjugates. Accordingly, immunochemical detection can be performed with a battery of antibody composites to identify the most appropriate combination of antibody components for subsequent in vivo diagnosis and therapy. For example, an antibody moiety that binds the c-erb B2 proto-oncogene product may be more suitable for a particular breast cancer than an antibody moiety that binds carcinoembryonic antigen. After a suitable combination of antibody components have been identified, further in vitro testing can be used to delineate the most efficacious linker size in the antibody composite, as discussed above.

Immunochemical detection can be performed by contacting a biological sample with an antibody composite and then contacting the biological sample with a detectably labeled molecule which binds to the antibody composite. For example, the detectably labeled molecule can comprise an antibody moiety that binds the antibody composite. Alternatively, the antibody composite can be conjugated with avidin/streptavidin (or biotin) and the detectably labeled molecule can comprise biotin (or avidin/streptavidin). Numerous variations of this basic technique are well-known to those of skill in the art.

Alternatively, an antibody composite can be conjugated with a diagnostic agent to form a polyspecific immunoconjugate. Antibody composites can be detectably labeled with any appropriate marker moiety, for example, a radioisotope, a fluorescent label, a chemiluminescent label, an enzyme label, a bioluminescent label or colloidal gold. Methods of making and detecting such detectably-labeled polyspecific immunoconjugates are well-known to those of ordinary skill in the art, and are described in more detail below.

The marker moiety can be a radioisotope that is detected by autoradiography. Isotopes that are particularly useful for the purpose of the present invention are $^3$H, $^{125}$I, $^{131}$I, $^{35}$S and $^{14}$C.

Polyspecific immunoconjugates also can be labeled with a fluorescent compound. The presence of a fluorescently-labeled antibody component is determined by exposing the polyspecific immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, polyspecific immunoconjugates can be detectably labeled by coupling an antibody component to a chemiluminescent compound. The presence of the chemiluminescent-tagged polyspecific immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label polyspecific immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, polyspecific immunoconjugates can be detectably labeled by linking an antibody component to an enzyme. When the polyspecific immunoconjugates-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to antibody components can be accomplished using standard techniques known to the art. Typical methodology in this regard is described by Kennedy et al., *Clin. Chim. Acta* 70: 1 (1976), Schurs et al., *Clin. Chim. Acta* 81: 1 (1977), Shih et al., *Int'l J. Cancer* 46: 1101 (1990), Stein et al., *Cancer Res.* 50: 1330 (1990), supra, and Stein et al., Int. J. Cancer 55: 938 (1993). Also, see generally, Coligan.

In addition, the convenience and versatility of immunochemical detection can be enhanced by using antibody components that have been conjugated with avidin, streptavidin, and biotin. See, for example, Wilchek et al. (eds.), *Avidin-Biotin Technology*, METHODS IN ENZYMOLOGY, VOL. 184 (Academic Press 1990), and Bayer et al., "Immunochemical Applications of Avidin-Biotin Technology," in METHODS IN MOLECULAR BIOLOGY, VOL. 10, Manson (ed.), pages 149–162 (The Human Press, Inc. 1992).

Thus, the above-described immunochemical detection methods can be used to assist in the diagnosis or staging of a pathological condition. These techniques also can be used to identify the most suitable composition of antibody composite or polyspecific immunoconjugate for subsequent in vivo diagnosis and therapy.

B. In Vivo Diagnosis

The present invention also contemplates the use of antibody composites and polyspecific immunoconjugates for in vivo diagnosis. The method of diagnostic imaging with radiolabeled MAbs is well-known. In the technique of immunoscintigraphy, for example, antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624–652 (Mack Publishing Co., 1990), Brown, "Clinical Use of Monoclonal Antibodies," in BIOTECHNOLOGY AND PHARMACY 227–49, Pezzuto et al. (eds.) (Chapman & Hall 1993), and Goldenberg, *CA—A Cancer Journal for Clinicians* 44: 43 (1994).

For diagnostic imaging, radioisotopes may be bound to an antibody composite either directly, or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313. Also, see Griffiths, U.S. Pat. No. 5,128,119 (1992).

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that can be bound to antibody composites and are appropriate for diagnostic imaging include γ-emitters and positron-emitters such as $^{99m}Tc$, $^{67}Ga$, $^{111}In$, $^{123}I$, $^{124}I$, $^{125}I$, $^{131}I$, $^{51}Cr$, $^{89}Zr$, $^{18}F$ and $^{68}Ga$. Other suitable radioisotopes are known to those of skill in the art.

Preferred γ-emitters have a gamma radiation emission peak in the range of 50–500 Kev, primarily because the state of the art for radiation detectors currently favors such labels. Examples of such γ-emitters include $^{99m}Tc$, $^{67}Ga$, $^{123}I$, $^{125}I$ and $^{131}I$.

Antibody composites also can be labeled with paramagnetic ions for purposes of in vivo diagnosis. Elements that are particularly useful for magnetic resonance imaging include Gd, Mn, Dy and Fe ions.

A high background level of non-targeted antibody provides a major impediment to in vivo diagnosis methodology. However, the ratio of target to nontarget radiolabeled antibody can be enhanced through the use of a nonlabeled second antibody which scavenges and promotes the clearance of the nontargeted circulating radiolabeled antibody. The second antibody may be whole IgG or IgM, or a fragment of IgG or IgM, so long as it is capable of binding the radiolabeled antibody to form a complex which is cleared from the circulation and nontarget spaces more rapidly than the radiolabeled antibody alone. In the present context, suitable second antibodies may bind with either the Fc portion or variable region of a radiolabeled polyspecific immunoconjugate. See, for example, Goldenberg, U.S. Pat. No. 4,624,846, Goldenberg, international publication No. WO 92/19273, and Sharkey et al., *Int. J. Cancer* 51: 266 (1992), which are incorporated by reference.

For example, the location of multidrug resistant (MDR) tumor cells, MDR HIV-infected cells or MDR infectious agents in a mammal having a multidrug resistant disease caused by a tumor or infectious agent can be determined by parenterally injecting the mammal with a polyspecific immunoconjugate comprising (1) at least one antibody component that binds with a first epitope of a multidrug transporter protein, (2) at least one antibody component that binds with a first epitope of an antigen that is associated with the tumor or infectious agent, and (3) a diagnostic agent. Subsequently, the mammal is injected with an antibody or antibody fragment that binds with the polyspecific immunoconjugate in an amount that is sufficient to decrease the level of circulating polyspecific immunoconjugate by about 10–85% within 2 to 72 hours. The mammal is then scanned with a detector to locate the site or sites of uptake of the polyspecific immunoconjugate. See Goldenberg, U.S. Pat. No. 4,624,846.

In an alternate approach, detection methods are improved by taking advantage of the binding between avidin/ streptavidin and biotin. Avidin, found in egg whites, has a very high binding affinity for biotin, which is a B-complex vitamin. Streptavidin, isolated from *Streptomyces avidinii*, is similar to avidin, but has lower non-specific tissue binding and therefore, streptavidin often is used in place of avidin. A basic diagnostic method comprises administering an antibody composite conjugated with avidin/streptavidin (or biotin), injecting a clearing composition comprising biotin (or avidin/streptavidin), and administering a conjugate of a diagnostic agent and biotin (or avidin/streptavidin). Preferably, the biotin (or avidin/streptavidin) component of the clearing composition is coupled with a carbohydrate moiety (such as dextran) or a polyol group (e.g., polyethylene glycol) to decrease immunogenicity and permit repeated applications.

A modification of the basic method is performed by parenterally injecting a mammal with an antibody composite which has been conjugated with avidin/streptavidin (or biotin), injecting a clearing composition comprising biotin (or avidin/streptavidin), and parenterally injecting a polyspecific immunoconjugate according to the present invention, which further comprises avidin/streptavidin (or biotin). See Goldenberg, international publication No. WO 94/04702, which is incorporated by reference.

In a further variation of this method, improved detection can be achieved by conjugating multiple avidin/streptavidin or biotin moieties to a polymer which, in turn, is conjugated to an antibody component. Adapted to the present invention, antibody composites or polyspecific immunoconjugates can be produced which contain multiple avidin/streptavidin or biotin moieties. Techniques for constructing and using multiavidin/multistreptavidin and/or multibiotin polymer conjugates to obtain amplification of targeting are disclosed by Griffiths, international application No. PCT/US94/04295, which is incorporated by reference.

In another variation, improved detection is achieved by injecting a targeting antibody composite conjugated to biotin (or avidin/streptavidin), injecting at least one dose of an avidin/streptavidin (or biotin) clearing agent, and injecting a diagnostic composition comprising a conjugate of biotin (or avidin/streptavidin) and a naturally occurring metal atom chelating protein which is chelated with a metal detection agent. Suitable targeting proteins according to the present invention would be ferritin, metallothioneins, ferredoxins, and the like. This approach is disclosed by Goldenberg et al., international application No. PCT/US94/05149, which is incorporated by reference.

Polyspecific immunoconjugates which comprise a radiolabel also can be used to detect multidrug resistant (MDR) tumor cells, MDR HIV-infected cells or MDR infectious agents in the course of intraoperative and endoscopic examination using a small radiation detection probe. See Goldenberg U.S. Pat. No. 4,932,412, which is incorporated by reference. As an illustration of the basic approach, a surgical or endoscopy subject is injected parenterally with a polyspecific immunoconjugate comprising (1) at least one antibody component that binds with a first epitope of a multidrug transporter protein, (2) at least one antibody component that binds with a first epitope of an antigen that is associated with a tumor or infectious agent, and (3) a radioisotope. Subsequently, the surgically exposed or endoscopically accessed interior of the body cavity of the subject is scanned at close range with a radiation detection probe to detect the sites of accretion of the polyspecific immunoconjugate.

In a variation of this method, a photoactive agent or dye, such as dihematoporphyrin ether (Photofrin II), is injected systemically and sites of accretion of the agent or dye are detected by laser-induced fluorescence and endoscopic imaging. See Goldenberg, international application No. PCT/US93/04098, which is incorporated by reference. The prior art discloses imaging techniques using certain dyes that are accreted by lesions, such as tumors, and which are in turn activated by a specific frequency of light. These methods are described, for example, in Dougherty et al., *Cancer Res.* 38: 2628 (1978); Dougherty, *Photochem. Photobiol.* 45: 879 (1987); Doiron et al. (eds.), PORPHYRIN LOCALIZATION AND TREATMENT OF TUMORS (Alan Liss, 1984); and van den Bergh, *Chem. Britain* 22: 430 (1986), which are incorporated herein in their entirety by reference.

In a basic technique, a subject is injected parenterally with a polyspecific immunoconjugate comprising (1) at least one antibody component that binds with a first epitope of a multidrug transporter protein, (2) at least one antibody component that binds with a first epitope of an antigen that is associated with a tumor or infectious agent, and (3) a photoactive agent or dye. Sites of accretion are detected using a light source provided by an endoscope or during a surgical procedure.

The detection of polyspecific immunoconjugate during intraoperative or endoscopic examination can be enhanced through the use of second antibody or avidin/streptavidin/biotin clearing agents, as discussed above.

In these endoscopic techniques the detection means can be inserted into a body cavity through an orifice, such as, the mouth, nose, ear, anus, vagina or incision. As used herein, the term "endoscope" is used generically to refer to any scope introduced into a body cavity, e.g., an anally introduced endoscope, an orally introduced bronchoscope, a urethrally introduced cystoscope, an abdominally introduced laparoscope or the like. Certain of these may benefit greatly from further progress in miniaturization of components and their utility to practice the method of the present invention will be enhanced as a function of the development of suitably microminiaturized components for this type of instrumentation. Highly miniaturized probes which could be introduced intravascularly, e.g., via catheters or the like, are also suitable for use in the embodiments of the invention for localizing MDR tumor cells, MDR HIV-infected cells or MDR infectious agents.

7. Use of Polyspecific Immunoconjugates and Antibody Composites for Therapy

The present invention also contemplates the use of antibody composites and polyspecific immunoconjugates for immunotherapy. An objective of immunotherapy is to deliver cytotoxic doses of radioactivity, toxin, or drug to target cells, while minimizing exposure to non-target tissues. The polyspecific immunoconjugates and antibody composites of the present invention are expected to have a greater binding specificity than multidrug transporter protein MAbs, since the polyspecific immunoconjugates and antibody composites comprise moieties that bind to at least one multidrug transporter protein epitope and an antigen associated with either a tumor or an infectious agent.

For example, a therapeutic polyspecific immunoconjugate may comprise an α-emitting radioisotope, a β-emitting radioisotope, a γ-emitting radioisotope, an Auger electron emitter, a neutron capturing agent that emits α-particles or a radioisotope that decays by electron capture. Suitable radioisotopes include $^{198}Au$, $^{32}P$, $^{125}I$, $^{131}I$, $^{90}Y$, $^{186}Re$, $^{188}Re$, $^{67}Cu$, $^{211}At$, and the like.

As discussed above, a radioisotope can be attached to an antibody composite directly or indirectly, via a chelating agent. For example, $^{67}Cu$, considered one of the more promising radioisotopes for radioimmunotherapy due to its 61.5 hour half-life and abundant supply of beta particles and gamma rays, can be conjugated to an antibody composite using the chelating agent, p-bromoacetamido-benzyl-tetraethylaminetetraacetic acid (TETA). Chase, supra. Alternatively, $^{90}$Y, which emits an energetic beta particle, can be coupled to an antibody composite using diethylenetriaminepentaacetic acid (DTPA). Moreover, a method for the direct radiolabeling of the antibody composite with $^{131}$I is described by Stein et al., *Antibody Immunoconj. Radiopharm.* 4: 703 (1991).

Alternatively, boron addends such as carboranes can be attached to antibody composites. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody composite. After administration of the polyspecific immunoconjugate, a boron addend is activated by thermal neutron irradiation and converted to radioactive atoms which decay by α-emission to produce highly toxic, short-range effects.

In addition, therapeutically useful polyspecific immunoconjugates can be prepared in which an antibody composite is conjugated to a toxin or a chemotherapeutic drug. Illustrative of toxins which are suitably employed in the preparation of such conjugates are ricin, abrin, human ribonuclease, pokeweed antiviral protein, gelonin, diphtherin toxin, and Pseudomonas endotoxin. See, for example, Pastan et al., *Cell* 47: 641 (1986), and Goldenberg, *CA—A Cancer Journal for Clinicians* 44: 43 (1994). Other suitable toxins are known to those of skill in the art.

Useful cancer chemotherapeutic drugs for the preparation of polyspecific immunoconjugates include nitrogen mustards, alkyl sulfonates, nitrosoureas, triazenes, folic acid analogs, pyrimidine analogs, purine analogs, antibiotics, epipodophyllotoxins, platinum coordination complexes, hormones, and the like. Chemotherapeutic drugs that are useful for treatment of infectious agents include antiviral drugs (such as AZT, 2',3'-dideoxyinosine and 2',3'-dideoxycytidine), antimalarial drugs (such as chloroquine and its congeners, diaminopyrimidines, mefloquine), antibacterial agents, antifungal agents, antiprotozoal agents, and the like. Suitable chemotherapeutic agents are described in REMINGTON'S PHARMACEUTICAL SCIENCES, 18th Ed. (Mack Publishing Co. 1990), and in GOODMAN AND GILMAN'S THE PHARMACOLOGICAL BASIS OF THERAPEUTICS, 7th Ed. (MacMillan Publishing Co. 1985), which are incorporated by reference. Other suitable chemotherapeutic agents, such as experimental drugs, are known to those of skill in the art.

In addition, therapeutically useful polyspecific immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion (cited above). In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22: 430 (1986)). Moreover, monoclonal antibodies have been coupled with photoactivated dyes for achieving phototherapy (Mew et al., *J. Immunol.* 130: 1473 (1983); idem., *Cancer Res.* 45: 4380 (1985); Oseroff et al., *Proc. Natl. Acad. Sci. USA* 83: 8744 (1986); idem., *Photochem. Photobiol.* 46: 83 (1987); Hasan et al., *Prog. Clin. Biol. Res.* 288: 471 (1989); Tatsuta et al., *Lasers Surg. Med.* 9: 422 (1989); Pelegrin et al., *Cancer* 67: 2529 (1991)—all incorporated in their entirety herein by reference). However, these earlier studies did not include use of endoscopic therapy applications, especially with the use of antibody fragments or subfragments. Thus, the present invention contemplates the therapeutic use of polyspecific immunoconjugates comprising photoactive agents or dyes. The general methodology is described above in relation to the use of such polyspecific immunoconjugates for diagnosis.

Moreover, therapeutically useful polyspecific immunoconjugates can be prepared in which an antibody composite is conjugated to a compound that reverses multidrug resistance. Such "chemosensitizing agents" include verapamil and its analogs, calmodulin antagonists, anthracycline and Vinca alkaloid analogs, and the like. See, for example, Endicott et al., *Ann. Rev. Biochem.* 58: 137 (1989), Ford et al., *Pharmacol. Rev.* 42: 155 (1990) and Calabresi et al., *PPO Updates* 8: 1 (1994). See also Sarkadi et al., *FASEB J.* 8: 766 (1994), which provides methods to identify hydrophobic peptide derivatives that reverse multidrug resistance. These polyspecific immunoconjugates may be administered prior to, or concurrent with, the administration of appropriate chemotherapeutic drugs.

As an alternative, unconjugated chemosensitizing agents may be administered with polyspecific immunoconjugates comprising a toxin or chemotherapeutic drug. Typical modes of administration and dosages of chemosensitizing agents are described, for example, by Presant et al., *Am. J. Clin. Oncol.* 9: 355 (1986), Cairo et al., *Cancer Res.* 49: 1063 (1989), Miller et al., *J. Clin. Oncol.* 9: 37 (1991) and Calabresi et al., supra, Rubin, U.S. Pat. No. 5,005,588, and Levy, U.S. Pat. No. 5,258,372, which are incorporated by reference.

In addition, therapeutic polyspecific immunoconjugates can comprise an immunomodulator moiety. As used herein, the term "immunomodulator" includes cytokines, stem cell growth factors, tumor necrosis factors (TNF) and hematopoietic factors, such as interleukins (e.g., interleukin-1 (IL-1), IL-2, IL-3, IL-6 and IL-10), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, interferon-', TNF-α, and the like.

Such polyspecific immunoconjugates provide a means to deliver an immunomodulator to a target cell and are particularly useful against tumor cells and mammalian cells that express an infectious agent antigen on the cell surface, such as HIV-infected cells. The cytotoxic effects of immunomodulators are well known to those of skill in the art. See, for example, Klegerman et al., "Lymphokines and Monokines," in BIOTECHNOLOGY AND PHARMACY, Pessuto et al. (eds.), pages 53–70 (Chapman & Hall 1993). As an illustration, type I interferons and interferon-γ induce an antiviral state in various cells by activating 2',5'-oligoadenylate synthetase and protein kinase. Moreover, interferons can inhibit cell proliferation by inducing increased expression of class I histocompatibility antigens on the surface of various cells and thus, enhance the rate of destruction of cells by cytotoxic T lymphocytes. Furthermore, tumor necrosis factors, such as TNF-α, are believed to produce cytotoxic effects by inducing DNA fragmentation.

The present invention also contemplates two-, three- or four-step targeting strategies to enhance antibody therapy.

General techniques include the use of antibody components conjugated with avidin, streptavidin or biotin, and the use of second antibodies that bind with the primary immunoconjugate, as discussed above. See, for example, Goodwin et al., *Eur. J. Nucl. Med.* 9:209 (1984), Goldenberg et al., *J. Nucl. Med.* 28:1604 (1987), Hnatowich et al., *J. Nucl. Med.* 28: 1294 (1987), Paganelli et al., *Cancer Res.* 51: 5960 (1991), Goldenberg, international publication No. WO 92/19273, Sharkey et al., *Int. J. Cancer* 51: 266 (1992), and Goldenberg, international application No. WO 94/04702, which are incorporated by reference. Also, see Griffiths, international application No. PCT/US94/04295, which describes a method using multiavidin and/or multibiotin polymer conjugates, and Goldenberg et al., international application No. PCT/US94/05149, which discloses improved methods for therapy with chelatable radiometals.

For example, a mammal having a multidrug resistant disease caused by a tumor or infectious agent may be treated by parenterally injecting the mammal with a polyspecific immunoconjugate comprising (1) at least one antibody component that binds with a first epitope of a multidrug transporter protein, (2) at least one antibody component that binds with a first epitope of an antigen that is associated with the tumor or infectious agent, and (3) a therapeutic agent. Subsequently, the mammal is injected with an antibody or antibody fragment that binds with the polyspecific immunoconjugate in an amount that is sufficient to decrease the level of circulating polyspecific immunoconjugate by about 10–85% within 2 to 72 hours.

In an alternative approach to enhancing the therapeutic index comprises administering an antibody composite conjugated with avidin/streptavidin (or biotin), injecting a clearing composition comprising biotin (or avidin/streptavidin), and administering a conjugate of a therapeutic agent and avidin/streptavidin (or biotin), as discussed above.

The present invention also contemplates a method of therapy using unconjugated antibody composites. Investigators have found that P-glycoprotein antibodies can restore drug sensitivity in multidrug resistant cultured cells and multidrug resistant human tumor xenografts in nude mice. Grauer et al., European patent application No. EP-0 569 141, Rittmann-Grauer et al., *Cancer Res.* 52: 1810 (1992), Pearson et al., *J. Nat'l Cancer Inst.* 83: 1386 (1991), and Iwahashi et al., *Cancer Res.* 53: 5475 (1993). P-glycoprotein antibodies also can inhibit the growth of multidrug resistant human xenografts in nude mice. Grauer et al., European patent application No. EP-0 569,141. Accordingly, the more specific antibody composites of the present invention provide an improved method to treat a mammal having a multidrug resistant disease caused by a tumor or infectious agent in which the multidrug resistant cells overexpress P-glycoprotein. Moreover, the antibody composites of the present invention can be used to inhibit active drug efflux in infectious agents and thus, restore sensitivity to chemotherapy.

Antibody composites may be administered alone, or in conjugation with the conventional chemotherapeutic agents described above. Modes of chemotherapeutic administration and suitable dosages are well known to those of skill in the art. See, for example, REMINGTON'S PHARMACEUTICAL SCIENCES, 18th Ed. (Mack Publishing Co. 1990), and GOODMAN AND GILMAN'S THE PHARMACOLOGICAL BASIS OF THERAPEUTICS, 7th Ed. (MacMillan Publishing Co. 1985).

In general, the dosage of administered polyspecific immunoconjugates and antibody composites will vary depending upon such factors as the patient's age, weight, height, sex, general medical condition and previous medical history. Typically, it is desirable to provide the recipient with a dosage of polyspecific immunoconjugate or antibody composite which is in the range of from about 1 pg/kg to 10 mg/kg (amount of agent/body weight of patient), although a lower or higher dosage also may be administered as circumstances dictate.

Administration of polyspecific immunoconjugates or antibody composites to a patient can be intravenous, intraarterial, intraperitoneal, intramuscular, subcutaneous, intrapleural, intrathecal, by perfusion through a regional catheter, or by direct intralesional injection. When administering polyspecific immunoconjugates or antibody composites by injection, the administration may be by continuous infusion or by single or multiple boluses.

Polyspecific immunoconjugates having a boron addend-loaded carrier for thermal neutron activation therapy will normally be effected in similar ways. However, it will be advantageous to wait until non-targeted polyspecific immunoconjugate clears before neutron irradiation is performed. Clearance can be accelerated using an antibody that binds to the polyspecific immunoconjugate. See U.S. Pat. No. 4,624,846 for a description of this general principle.

The polyspecific immunoconjugates and antibody composites of the present invention can be formulated according to known methods to prepare pharmaceutically useful compositions, whereby polyspecific immunoconjugates or antibody composites are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

For purposes of therapy, a polyspecific immunoconjugate (or antibody composite) and a pharmaceutically acceptable carrier are administered to a patient in a therapeutically effective amount. A combination of a polyspecific immunoconjugate (or antibody composite) and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent is physiologically significant if its presence results in the inhibition of the growth of target cells, or in the increased susceptibility of target cells to a chemotherapeutic agent.

Additional pharmaceutical methods may be employed to control the duration of action of a polyspecific immunoconjugate or antibody composite in a therapeutic application. Control release preparations can be prepared through the use of polymers to complex or adsorb the polyspecific immunoconjugate or antibody composite. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of a polyspecific immunoconjugate (or antibody composite) from such a matrix depends upon the molecular weight of the polyspecific immunoconjugate (or antibody composite), the amount of polyspecific immunoconjugate (or antibody composite) within the matrix, and the size of dispersed particles. Saltzman et al., *Biophys. J.* 55: 163 (1989); Sherwood et al., supra. Other solid dosage forms are described in REMINGTON'S PHARMACEUTICAL SCIENCES, 18th ed. (1990).

The present invention also contemplates a method of treatment in which immunomodulators are administered to prevent, mitigate or reverse radiation-induced or drug-induced toxicity of normal cells, and especially hematopoietic cells. Adjunct immunomodulator therapy allows the administration of higher doses of cytotoxic agents due to increased tolerance of the recipient mammal. Moreover, adjunct immunomodulator therapy can prevent, palliate, or reverse dose-limiting marrow toxicity. Examples of suitable immunomodulators for adjunct therapy include G-CSF, GM-CSF, thrombopoietin, IL-1, IL-3, and the like. The method of adjunct immunomodulator therapy is disclosed by Goldenberg, U.S. Pat. No. 5,120,525, which is incorporated by reference.

Those of skill in the art are aware that an antibody component is just one example of a moiety that can be used to target particular cells. Other useful targeting moieties include non-antibody proteins, peptides, polypeptides, glycoproteins, lipoproteins, or the like, e.g., growth factors, enzymes, receptor proteins, immunomodulators and hormones. For example, Sarkadi et al., *The FASEB Journal* 8: 766 (1994), which is incorporated by reference, provides methods for identifying hydrophobic peptides that interact with P-glycoprotein. As an illustration, a polyspecific conjugate suitable for diagnosis and/or treatment of certain multidrug resistant breast cancers would comprise a hydrophobic peptide that binds with P-glycoprotein, an epidermal growth factor moiety that binds with the c-erb B2 proto-oncogene product, and a diagnostic or therapeutic agent.

The present invention, thus generally described, will be understood more readily by reference to the following examples, which are provided by way of illustration and are not intended to be limiting of the present invention.

EXAMPLE 1

Production of Antibody Components: Murine P-Glycoprotein MAb and Anti-CEA MAb

1. Production of Monoclonal Antibodies

Methods for producing anti-P-glycoprotein murine monoclonal antibodies are well-known to those of skill in the art, as discussed above. One approach is to immunize mice with cells, or cellular membranes, that contain an abundance of P-glycoprotein. Cells that over-express P-glycoprotein can be obtained by selecting and enriching cells that express the MDR phenotype from a human continuous cell line. See, for example, Gottesman, "Drug-Resistant Mutants: Selection and Dominance Analysis," in METHODS IN ENZYMOLOGY, VOL. 151, Colowick et al., (eds.), pages 113–121 (Academic Press 1987), and Clynes et al., *Cytotechnology* 12: 231 (1993).

A general method for using MDR cells to produce anti-P-glycoprotein monoclonal antibodies is described, for example, by Rittmann-Grauer et al., *Cancer Res.* 52: 1810 (1992), which is incorporated by reference. Briefly, six week old female BALB/c mice are injected intraperitoneally (i.p.) with 5×10⁶ MDR cells that have been scraped from the surface of tissue culture flasks. Three weeks later, mice receive a second i.p. injection of 5×10⁶ MDR cells. Four days prior to fusion, mice receive a final intravenous boost of 5×10⁶ MDR cells. Splenocytes from the immunized mice are fused with murine myeloma cells, SP2/0-Ag 14, according to the method of Gerhard, "Fusion of Cells in Suspension and Outgrowth of Hybrids in Conditioned Medium," in MONOCLONAL ANTIBODIES, Kennet et al. (eds.), pages 370–371 (Plenum Publishing Corp. 1981).

Anti-P-glycoprotein hybridoma cultures are initially screened using an indirect ELISA with a horseradish peroxidase conjugate of goat anti-mouse immunoglobulin. Monolayers of the MDR cells and the drug-sensitive parental cell line are cultured in 96-well microtiter plates. Cells are fixed with 0.01% glutaraldehyde for 45 minutes at room temperature, the fixative is removed, cells are washed three times with phosphate-buffered saline (PBS), and the microtiter wells are blocked with 10% bovine serum albumin for at least 45 minutes. Fifty microliters of hybridoma supernatants are added to the microtiter wells and allowed to incubate for one hour at 37° C. Plates are then washed with PBS and incubated with 50 µl of peroxidase-conjugated goat anti-mouse immunoglobulin diluted 1:1000 in PBS with 10% horse serum. Following five washes with PBS, positive clones are identified by the addition of 100 µl of a solution containing 1 mg/ml O-phenylenediamine, 0.1% hydrogen peroxide, 50 mM citrate, and 100 mM sodium phosphate buffer (pH 5.0). The reaction is quenched by the addition of 50 µl 4N sulfuric acid, and the plates are read at 490 nm.

Clones that produce a five-fold or greater ELISA signal for the MDR cells, compared with drug-sensitive cells, are expanded. Hybridoma cells that produce anti-P-glycoprotein antibodies are injected into BALB/c mice for ascites production according to the procedure of Hoogenraad et al., *J. Immunol. Methods* 61: 317 (1983). Anti-P-glycoprotein antibodies are purified from the ascites fluid using protein A chromatography. See, for example, Langone et al., *J. Immunol. Methods* 51: 3 (1982).

The production of highly specific anti-CEA MAb, has been described by Hansen et al., *Cancer* 71: 3478 (1993), which is incorporated by reference. Briefly, a 20 gram BALB/c female mouse was immunized subcutaneously with 7.5 µg of partially-purified CEA in complete Freund adjuvant. On day 3, the mouse was boosted subcutaneously with 7.5 µg of CEA in incomplete Freund adjuvant and then, the mouse was boosted intravenously with 7.5 µg of CEA in saline on days 6 and 9. On day 278, the mouse was given 65 µg of CEA intravenously in saline and 90 µg of CEA in saline on day 404. On day 407, the mouse was sacrificed, a cell suspension of the spleen was prepared, the spleen cells were fused with murine myeloma cells, SP2/0-Ag 14 (ATCC CRL 1581) using polyethylene glycol, and the cells were cultured in medium containing 8-azaguanine. Hybridoma supernatants were screened for CEA-reactive antibody using an $^{125}$I-CEA radioimmunoassay (Roche; Nutley, N.J.). Positive clones were recloned.

2. The Production of Antibody Fragments

As described above, proteolysis provides one method for preparing antibody fragments. This technique is well-known to those of skill in the art. For example, see Coligan et al., supra, at pp. 2.8.1–2.8.10. Also see Stanworth et al. "Immunochemical Analysis of Human and Rabbit Immunoglobulins and Their Subunits," in HANDBOOK OF EXPERIMENTAL IMMUNOLOGY, Vol. 1, Weir (ed.), pages 12.1–12.46 (Blackwell Scientific 1986), and Parham, "Preparation and Purification of Active Fragments from Mouse Monoclonal Antibodies," Id. at pages 14.1–14.23.

As an example, preactivated papain can be used to prepare F(ab)₂ fragments from IgG1 or Fab fragments from IgG2a and IgG2b, as follows. Papain is activated by incubating 2 mg/ml papain (2× recrystallized suspension, Sigma #P3125) and 0.05M cysteine (free-base, crystalline; Sigma #C7755) for 30 minutes in a 37° C. water bath. To remove cysteine, the papain/cysteine mixture is applied to a PD-10 column (Pharmacia #G-25), which has been equilibrated with 20 ml of acetate/EDTA buffer (0.1M acetate with 3 mM EDTA, pH 5.5). Fractions are assayed by measuring absorbance at 280 nm, and the two or three fractions that contain protein are pooled. The concentration of preactivated papain is determined by using the formula: (absorbance at 280 nm)/2.5= mg. preactivated papain/ml.

To prepare antibody for digestion, 10 mg of antibody in 2 to 5 ml of PBS are dialyzed against acetate/EDTA buffer. Five hundred micrograms of preactivated papain are added to the dialyzed antibody solution, and the mixture is vortexed. After a 6–12 hour incubation in a 37° C. water bath, papain is inactivated by adding crystalline iodoacetamide (Sigma #I6125) to a final concentration of 0.03M. The mixture is then dialyzed against 1 liter of PBS (pH 8.0) at 4° C. for 6–12 hours.

To remove undigested antibody and Fc fragments, the mixture is applied to a protein A-Sepharose column which has been equilibrated in PBS (pH 8.0). Unbound fractions are collected in 2 ml aliquots and pooled. After concentrating the pool to a total volume of 5 ml or less, protein is fractionated by size-exclusion chromatography and the results are analyzed by SDS-PAGE.

EXAMPLE 2

Preparation of Antibody Composite: Anti-P-Glycoprotein/anti-CEA Bispecific Antibody A bispecific F(ab')$_2$ antibody composite is prepared from an Fab' fragment of an anti-P-glycoprotein monoclonal antibody and an Fab' fragment of a monoclonal antibody specific for CEA, using the methods described above. Also, see Goldenberg, international publication No. WO 92/19273, which is incorporated by reference. Briefly, the interchain disulfide bridges are reduced carefully with cysteine, taking care to avoid light-heavy chain cleavage, to form Fab'-SH fragments. The SH group(s) of one antibody fragment is(are) activated with an excess of bis-maleimide linker (1,1'-(methylenedi-1,4-phenylene)bismaleimide (Aldrich Chemical Co.; Milwaukee, Wis.). The second antibody fragment is also converted to Fab'-SH and then reacted with the activated first antibody fragment to obtain a bispecific antibody composite.

EXAMPLE 3

Preparation of Polyspecific Immunoconjugate

A polyspecific immunoconjugate can be prepared by binding a therapeutic or diagnostic agent to the bispecific antibody composite, described in Example 2. As an example, the anti-P-glycoprotein/anti-CEA composite can be conjugated with doxorubicin via dextran, using the method of Shih et al., *Int. J. Cancer* 41:832–839 (1988). Briefly, amino dextran is prepared by dissolving one gram of dextran (m.w. 18 kD; Sigma Chemical Co.; St. Louis, Mo.) in 70 ml of water. The dextran is partially oxidized to form polyaldehyde dextran by adding 0.5 gram of sodium metaperiodate, and stirring the solution at room temperature overnight. After concentrating the mixture with an Amicon cell (YM10 membrane; MWCO=10,000), the polyaldehyde dextran is purified by Sephadex G-25 chromatography and lyophilized to give about 900 grams of white powder. Polyaldehyde dextran is then treated with two equivalents of 1,3-diamino-2-hydroxypropane in aqueous phase for 24 hours at room temperature. The resultant Schiff base is stabilized by addition of sodium borohydride (0.311 mmol per 2.15 mmol of 1,3-diamino-2-hydroxypropane) to the mixture. The mixture is allowed to incubate at room temperature for six hours. Amino dextran is purified using a Sephadex G-25 column.

Doxorubicin (Sigma Chemical Co.; St. Louis, Mo.) is activated by adding one milliliter of anhydrous DMF to 0.1 mmole of doxorubicin in a dried Reacti-vial, followed by a solution of N-hydroxysuccinimide (23 mg, 0.2 mmole; Sigma) in 750 μl of anhydrous DMF and a solution of 1,3-dicyclohexylcarbodiimide (41.5 mg, 0.2 mmol; Sigma) in 750 μl of anhydrous DMF. The reaction mixture is stirred in the dark at room temperature for 16 hours under anhydrous conditions. The precipitate is then centrifuged and the solution is stored in a sealed bottle at −20° C.

Doxorubicin-dextran intermediate conjugate is prepared by dissolving aminodextran (18 kD; 10 mg) in two milliliters of PBS (pH 7.2) and gradually adding 0.7 ml of the above N-hydroxy-succinimide-activated doxorubicin solution. Thus, 50 moles of doxorubicin are present per mole of aminodextran. The solution is stirred at room temperature for five hours and after removing any precipitate, the conjugate is purified using a Sephadex G-25 column. Doxorubicin-dextran conjugate is typically characterized by a doxorubicin/dextran ratio of 14.

Alternatively, doxorubicin-dextran conjugate is prepared by reacting doxorubicin with 1-ethyl-3(3-dimethylaminopropyl)-carbodiimide, as described by Shih et al., *Int. J. Cancer* 41:832–839 (1988). Also, see Shih et al., *Cancer Research* 51:4192–4198 (1991).

The bispecific antibody conjugate (25 mg) in 5 ml of PBS (pH 5.5) is oxidized in the dark by treatment with sodium metaperiodate (800 μl of a 21.5 mg/ml solution) at room temperature for 60 minutes. The reaction mixture is then treated with ethylene glycol (50 μl) to decompose the unreacted periodate and the oxidized antibody fragment is purified using a Sephadex G-25 column equilibrated in 0.05M HEPES (pH 7.4). Subsequently, the oxidized fragment is concentrated to 5 mg/ml in 0.05M HEPES (pH 7.4) and reacted with the doxorubicin-dextran conjugate (22 mg). After 24 hours at room temperature, the Schiff base is reduced by NaBH$_3$CN. Conjugated antibody is purified using a Sepharose CL-6B column.

EXAMPLE 4

Preparation of an Polyspecific Immunoconjugate Comprising a Radioisotope

A polyspecific immunoconjugate can be prepared in which a radioisotope is bound to one or more antibody components via a chelator. As an illustration, the antibody composite of Example 2 may be conjugated with either aminobenzyl diethylenetriaminepentaacetic acid (DTPA) or a derivative of DTPA containing the long-chain linker, —CSNH(CH$_2$)$_{10}$NH$_2$ (LC-DTPA). Briefly, the antibody composite (2.5 mg in about one milliliter of 50 mM acetate-buffered 0.9% saline [ABS; pH 5.3]) is oxidized in the dark by treatment with sodium metaperiodate (210 μl of a 5.68 mg/ml solution) at 0° C. for one hour. The reaction mixture is treated with ethylene glycol (20 μl) to decompose the unreacted periodate and the oxidized antibody fragment is purified using a Sephadex G-50/80 column (Pharmacia; Piscataway, N.J.) equilibrated in PBS (pH 6.1). The oxidized fragment is then reacted with excess DTPA or LC-DTPA. After 40 hours at room temperature, the Schiff base is reduced by NaBH$_3$CN. Conjugated antibody composite is then purified using a centrifuged size-exclusion column (Sephadex G-50/80) equilibrated in 0.1M acetate (pH 6.5). The concentrations of antibody conjugates are determined by measuring absorbance at 280 nm.

The ratio of chelator molecules per molecule of antibody composite is determined by a metal-binding assay. The assay is performed by mixing an aliquot of the antibody conjugate with 0.1M ammonium acetate (pH 7) and 2M triethanolamine, and incubating the mixture at room temperature with a known excess of cobalt acetate spiked with $^{57}$cobalt acetate. After 30 minutes, EDTA (pH 7) is added to a final concentration of 10 mM. After a further 10 minute incubation, the mixture is analyzed by instant thin layer chromatography (ITLC) using 10 mM EDTA for development. The fraction of radioactivity bound to antibody is determined by counting sections of ITLC strips on a gamma counter. Typically, the results will show that there are about 6 molecules of DTPA per antibody component and about 5 molecules of LC-DTPA per antibody component.

Antibody conjugates are labeled with $^{90}$yttrium, as follows. Briefly, commercially available $^{90}$yttrium chloride (DuPont NEN; 17.68 µl; 5.63 mCi) is buffered with 35.4 µl of 0.5M acetate (pH 6.0). The solution is allowed to stand for 5–10 minutes at room temperature, and then used for radiolabeling.

$^{90}$Yttrium-labeled antibody composite-DTPA is prepared by mixing $^{90}$yttrium acetate (128.7 µCi) with antibody composite-DTPA (30 µg; 8.3 µl), incubating at room temperature for one hour, and diluting with 90 µl of 0.1M acetate (pH 6.5). $^{90}$Yttrium-labeled antibody composite-LC-DTPA is prepared by mixing $^{90}$yttrium acetate (109.5 µCi) with antibody composite-LC-DTPA (30 µg; 7.6 µl), incubating at room temperature for one hour, and diluting with 90 µl of 0.1M acetate (pH 6.5).

The extent of $^{90}$yttrium incorporation can be analyzed by incubating the labeling mixture with 10 mM EDTA for ten minutes, followed by ITLC examination using 10 mM EDTA for development. In this assay, unbound $^{90}$yttrium migrates with the solvent front, while antibody-bound $^{90}$yttrium remains at the origin. The presence of any colloidal $^{90}$yttrium is assayed by ITLC (co-spotted with human serum albumin) using a water:ethanol:ammonia (5:2:1) solution for development. In this system, the fraction of radioactivity at the origin represents colloidal $^{90}$yttrium. In addition, all labeling mixtures may be analyzed using radio-high pressure liquid chromatography. Typically, 90 to 96% of $^{90}$yttrium is incorporated into the resultant polyspecific immunoconjugate.

EXAMPLE 5

Treatment of Colon Cancer with $^{90}$Yttrium-Labeled Polyspecific Immunoconjugate and G-CSF A patient has a carcinoembryonic antigen (CEA) blood titer of 55 ng/ml due to peritoneal spread of a colon cancer which had been resected two years earlier and found to be a Dukes' C lesion. Since previous chemotherapy with fluorouracil had been unsuccessful, the patient presents for experimental therapy. The patient is given a 35 mCi dose of the $^{90}$yttrium-labeled polyspecific immmunoconjugate prepared in Example 4, by intraperitoneal injection. Two days later, an infusion of 5 µg/kg G-CSF (such as NEUPOGEN [Amgen, Inc.; Thousand Oaks, Calif.]) is instituted intravenously, and the patient's hematologic values are monitored thereafter. No significant drop in white blood cell count is noted, thus permitting a repetition of the radioimmunotherapy three weeks later, followed again by G-CSF therapy. A third treatment is given two months later, and radiological evidence of some tumor and ascites reduction is noted four weeks later. Thus, the patient is able to tolerate higher and more frequent doses of the radioimmunotherapy agent.

EXAMPLE 6

Preparation of an Antibody Composite Targeted to Multidrug Resistant *Psuedomonas Aeruginosa*

Those of skill in the art can use standard methods to produce antibodies against a multidrug transporter protein of an infectious agent. As an illustration, a bispecific antibody can be constructed which is targeted to multidrug resistant *Psuedomonas aeruginosa*. Antibody components that bind to OprK, a multidrug transporter protein of *Psuedomonas aeruginosa*, can be obtained using OprK protein that is overexpressed by bacterial cells. For example, the OprK gene can be synthesized using mutually priming long oligonucleotides which are based upon the nucleotide sequence disclosed in Poole et al., *J. Bacteriol.* 175: 7363 (1993). See, for example, Ausubel et al. (eds.), CURRENT PROTOCOLS IN MOLECULAR BIOLOGY, pages 8.2.8 to 8.2.13 (Wiley Interscience 1990). Also, see Wosnick et al., *Gene* 60:115 (1987). Moreover, current techniques using the polymerase chain reaction provide the ability to synthesize genes as large as 1.8 kilobases in length. Adang et al., *Plant Molec. Biol.* 21:1131 (1993); Bambot et al., *PCR Methods and Applications* 2:266 (1993).

The OprK gene is then cloned into a prokaryotic expression vector which is subsequently introduced into competent *E. coli* cells, using standard techniques. See, for example, Ausubel et al., supra, at pages 16.1.1–16.7.8. OprK protein is isolated from the host cells using standard techniques. (Id.)

Alternatively, OprK protein can be isolated from *Psuedomonas aeruginosae* which have been selected for the multidrug resistant phenotype, as described by Poole et al., supra.

Isolated OprK protein is used to generate anti-OprK MAb, as described above. Also, see Mole et al., "Production of Monoclonal Antibodies Against Fusion Proteins Produced in *Eschericia coli,*" in DNA CLONING, VOLUME III: A PRACTICAL APPROACH, Glover (ed.), pages 113–139 (IRL Press 1987), and Dean "Preparation and Testing of Monoclonal Antibodies to Recombinant Proteins," in METHODS IN MOLECULAR BIOLOGY, VOLUME 10: IMMUNOCHEMICAL PROTOCOLS, Manson (ed.) pages 43–63 (The Humana Press, Inc. 1992).

Thus, anti-OprK MAb, or a fragment thereof, provides one antibody component of a bispecific antibody. The second antibody component, which binds with a different antigen associated with the exterior surface of *Psuedomonas aeruginosa*, may be obtained using the general techniques described above. Alternatively, suitable monoclonal antibodies can be purchased from American Type Culture Collection (Rockville, Md.), such as antibodies against *Psuedomonas aeruginosa* lipopolysaccharide (ATCC CRL Nos. 8753, 8754, 8795, 8796 and 8797), lipoprotein H2 of the outer envelop of *Psuedomonas aeruginosa* (ATCC CRL 1783), *Psuedomonas aeruginosa* type a flagella (ATCC HB 9130), and *Psuedomonas aeruginosa* type b flagella (ATCC HB 9129).

An antibody composite comprising a moiety that binds OprK and a moiety that binds an exterior surface antigen of *P. aeruginosa* can be prepared using the methods described in Example 2.

EXAMPLE 7

Preparation and Use of an $^{111}$Indium-Labeled Polyspecific Immunoconjugate Targeted to Multidrug Resistant *Psuedomonas Aeruginosa*

Antibody composite-chelator conjugates are prepared as described in Example 4. The conjugates are labeled with $^{111}$Indium, as follows. Briefly, $^{111}$Indium chloride is buffered at pH 5.5 using ammonium acetate such that the final acetate concentration is about 0.2M. $^{111}$Indium acetate is added to a solution of the antibody composite-chelator conjugate in 0.1M acetate (pH 6.5), and the mixture is incubated for about one hour. Typically, reaction mixtures contain either 10 µg of antibody composite-DTPA and 73 µCi of $^{111}$Indium, or 10 µg of antibody composite-LC-DTPA and 126.7 µCi of $^{111}$Indium. The extent of $^{111}$Indium incorporation is analyzed using ITLC, as described above.

A patient with granulocytopenia has *Pseudomonas aeruginosa* pneumonia which is no longer responsive to carbenicillin treatment. Four millicuries of $^{111}$Indium-labeled polyspecific immmunoconjugate are injected intravenously and after waiting at least 24 hours, the patient is scanned with a gamma camera. Foci of increased radioactivity appear as nodes in the lower lobes of the lung, indicating the presence of pneumonic infiltrates with multidrug resistant *Pseudomonas aeruginosa*. A course of therapy is designed in which an aminoglycoside and carbenicillin are administered with nonradioactive polyspecific immunoconjugate that comprises an OprK-binding moiety, a moiety that binds an exterior surface antigen of *Pseudomonas aeruginosa* and a chemosensitizing agent.

EXAMPLE 8

Preparation of a $^{99m}$Tc-Labeled Polyspecific Immunoconjugate Targeted to Multidrug Resistant *Psuedomonas Aeruginosa*

An antibody composite is prepared which binds OprK and E87 antigen, an exterior surface antigen of *Psuedomonas aeruginosa*. General techniques for preparing the antibody composite are described in Example 6, and preparation of anti-E87 monoclonal antibodies is described by Sawada et al., U.S. Pat. No. 5,089,262.

The antibody composite is labeled with $^{99m}$Tc using methods that are well-known to those of skill in the art. See, for example, Crockford et al., U.S. Pat. No. 4,424,200, Paik et al., U.S. Pat. No. 4,652,440, Baidoo et al., *Cancer Research (Suppl.)* 50: 799s (1990), Griffiths et al., *Cancer Research* 51: 4594 (1991), Pak et al., U.S. Pat. No. 5,053,493, Griffiths et al., U.S. Pat. No. 5,128,119, Lever et al., U.S. Pat. No. 5,095,111, and Dean et al., U.S. Pat. No. 5,180,816.

As an illustration, $^{99m}$Tc-labeled polyspecific immunoconjugate can be obtained as described by Hansen et al., U.S. Pat. No. 5,328,679. Briefly, a solution of 0.075M SnCl$_2$ (solution I) is prepared by dissolving 3350 mg SnCl.2H$_2$O in one milliliter of 6N HCl and diluting the resultant solution with sterile H$_2$O which has been purged with argon. A solution of 0.1M NaK tartrate in 0.05M NaAc (pH 5.5) [solution II] is prepared with sterile H$_2$O purged with argon. One volume of solution I is mixed with 26 volumes of solution II, and the resultant solution III is filter sterilized and purged with argon.

A solution of antibody composite is reduced with 20 mM cysteine, and excess cysteine is removed by gel filtration. The reduced antibody composite (2 mg/ml) is stabilized at pH 4.5 in 0.05M NaOAc buffer containing 0.15M saline. The resultant solution IV is filter sterilized and purged with argon. Solution IV is mixed with a sufficient amount of solution III to obtain a final concentration of 123 µg Sn per mg of reduced antibody composite. The resultant solution V is adjusted to a pH of 4.5–4.8.

A sterile solution of sodium pertechnetate (10 mCi) in saline is added to an aliquot of solution V which contains 1.25 mg antibody composite and stable stannous ions, and the mixture is gently agitated. Labeling is quantitative within 5 minutes. The resultant solution of $^{99m}$Tc-labeled polyspecific immunoconjugate is ready for immediate injection.

The $^{99m}$Tc-labeled polyspecific immunoconjugate is administered to a subject, and sites of infection caused by multidrug resistant *Psuedomonas aeruginosa* are localized using single-photon emission computed tomography. Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A polyspecific immunoconjugate comprising:
   (a) at least one antibody component that binds with a first epitope of a multidrug transporter protein;
   (b) at least one antibody component that binds with a first epitope of an antigen, wherein said antigen is associated with a tumor or an infectious agent; and
   (c) at least one diagnostic or therapeutic agent.

2. The polyspecific immunoconjugate of claim 1, wherein said antibody components are selected from the group consisting of:
   (a) a murine monoclonal antibody;
   (b) a humanized antibody derived from (a);
   (c) a human monoclonal antibody;
   (d) a subhuman primate antibody; and
   (e) an antibody fragment derived from (a), (b), (c) or (d).

3. The polyspecific immunoconjugate of claim 2, wherein said antibody fragment is selected from the group consisting of F(ab')$_2$, F(ab)$_2$, Fab', Fab, Fv, sFv and minimal recognition unit.

4. The polyspecific immunoconjugate of claim 3, wherein said multidrug transporter protein is selected from the group consisting of P-glycoprotein, OtrB, Tel(L), Mmr, ActII, TcmA, NorA, QacA, CmlA, Bcr, EmrB, EmrD, AcrE, EnvD, MexB, Smr, QacE, MvrC, MsrA, DrrA, DrrB, TlrC, Bmr, TetA and OprK.

5. The polyspecific immunoconjugate of claim 4, wherein said diagnostic agent is selected from the group consisting of radioactive label, photoactive agent or dye, florescent label, enzyme label, bioluminescent label, chemiluminescent label, colloidal gold and paramagnetic ion.

6. The polyspecific immunoconjugate of claim 5, wherein said radioactive label is selected from the group consisting of γ-emitters and positron-emitters.

7. The polyspecific immunoconjugate of claim 6, wherein said γ-emitters have a gamma radiation emission peak in the range of 50–500 Kev.

8. The polyspecific immunoconjugate of claim 7, wherein said γ-emitters with a gamma radiation emission peak in the range of 50–500 Kev are selected from the group consisting of $^{99m}$Tc, $^{67}$Ga, $^{123}$I, $^{125}$I and $^{131}$I.

9. The polyspecific immunoconjugate of claim 4, wherein said therapeutic agent is selected from the group consisting of radioisotope, boron addend, immunomodulator, toxin, photoactive agent or dye, cancer chemotherapeutic drug, antiviral drug, antifungal drug, antibacterial drug, antiprotozoal drug and chemosensitizing agent.

10. The polyspecific immunoconjugate of claim 9, wherein said radioisotope is selected from the group consisting of α-emitters, β-emitters, γ-emitters, Auger electron emitters, neutron capturing agents that emit α-particles and radioisotopes that decay by electron capture.

11. The polyspecific immunoconjugate of claim 9, wherein said radioisotope is selected from the group consisting of $^{198}$Au, $^{32}$P, $^{125}$I, $^{131}$I, $^{90}$Y, $^{186}$Re, $^{188}$Re, $^{67}$Cu and $^{211}$At.

12. The polyspecific immunoconjugate of claim 4, further comprising an antibody component that binds with a second epitope of said multidrug transporter protein.

13. The polyspecific immunoconjugate of claim 12, further comprising an antibody component that binds with a second epitope of said tumor or infectious agent associated antigen, or with an epitope of a second antigen associated with said tumor or said infectious agent.

14. The polyspecific immunoconjugate of any one of claims 4, 12 or 13, further comprising an immunomodulator, wherein said immunomodulator is selected from the group consisting of cytokines, stem cell growth factors and hematopoietic factors.

* * * * *